US008262573B2

(12) United States Patent
Tsuda et al.

(10) Patent No.: US 8,262,573 B2
(45) Date of Patent: Sep. 11, 2012

(54) ULTRASONIC DIAGNOSIS APPARATUS, RADIOFREQUENCY WAVE CAUTERY TREATMENT DEVICE, ULTRASONIC DIAGNOSIS AND TREATMENT SYSTEM, AND ULTRASONIC DIAGNOSIS AND TREATMENT APPARATUS

(75) Inventors: Masaki Tsuda, Tokyo (JP); Takao Jibiki, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 939 days.

(21) Appl. No.: 12/329,000

(22) Filed: Dec. 5, 2008

(65) Prior Publication Data
US 2009/0149754 A1  Jun. 11, 2009

(30) Foreign Application Priority Data
Dec. 7, 2007 (JP) ................................. 2007-317111

(51) Int. Cl.
*A61B 8/00* (2006.01)
(52) U.S. Cl. ........................................................ 600/439
(58) Field of Classification Search .................. 600/437, 600/439
See application file for complete search history.

(56) References Cited

U.S. PATENT DOCUMENTS

| 5,224,482 A | 7/1993 | Nikoonahad et al. |
| 5,788,636 A * | 8/1998 | Curley ........................... 600/439 |
| 5,938,611 A | 8/1999 | Muzilla et al. |
| 5,964,706 A | 10/1999 | Mo et al. |
| 5,997,480 A | 12/1999 | Sumanaweera et al. |
| 6,213,947 B1 | 4/2001 | Phillips |
| 6,535,835 B1 | 3/2003 | Rubin et al. |
| 6,953,434 B2 | 10/2005 | Hao et al. |
| 2003/0109802 A1 * | 6/2003 | Laeseke et al. ............... 600/564 |

FOREIGN PATENT DOCUMENTS

JP  2007-135988  6/2007

* cited by examiner

*Primary Examiner* — Tse Chen
*Assistant Examiner* — Peter Luong
(74) *Attorney, Agent, or Firm* — Armstrong Teasdale LLP

(57) ABSTRACT

An ultrasonic diagnosis and treatment system includes an ultrasonic probe for transmitting and for receiving ultrasonic waves; an image generator unit for generating an ultrasonic image based on the echo signals received by the ultrasonic probe; a display unit for displaying an ultrasonic image generated by the image generator unit; and a biopsy needle for radiating radiofrequency waves. The ultrasonic diagnosis and treatment system includes a display controller unit for displaying on the display unit an ultrasonic image at the time of non-radiation of the radiofrequency waves generated based on the echo signals received by the ultrasonic probe at the time when the radiofrequency waves are not radiated from the biopsy needle, in place of the ultrasonic image at the time of radiation of the radiofrequency waves generated based on the echo signals received by the biopsy needle at the time of radiating the radiofrequency wave from the biopsy needle.

20 Claims, 15 Drawing Sheets

ULTRASONIC DIAGNOSIS APPARATUS, RADIOFREQUENCY WAVE CAUTERY TREATMENT DEVICE, ULTRASONIC DIAGNOSIS AND TREATMENT SYSTEM, AND ULTRASONIC DIAGNOSIS AND TREATMENT APPARATUS

CROSS REFERENCE TO RELATED APPLICATIONS

This application claims the benefit of Japanese Patent Application No. 2007-317111 filed Dec. 7, 2007, which is hereby incorporated by reference in its entirety.

BACKGROUND OF THE INVENTION

The embodiments described herein are is related to an ultrasonic diagnosis apparatus, a radiofrequency wave cautery treatment device, an ultrasonic diagnosis and treatment system which is capable of performing the cautery treatment by using the radiofrequency wave, and an ultrasonic diagnosis and treatment apparatus.

In an ultrasonic diagnosis and treatment system which is capable of performing the cautery treatment by using the radiofrequency wave, a biopsy needle is inserted into a subject while confirming on an ultrasonic image to conduct the cautery treatment of for example a tumor by radiating radiofrequency waves from the biopsy needle (see for example Japanese Unexamined Patent Publication No. 2007-135988). In such an ultrasonic diagnosis and treatment system, the biopsy needle is inserted while viewing an ultrasonic image on the real time basis, so that the transmission and the reception of the ultrasonic waves from an ultrasonic probe for generating the ultrasonic image is performed at the same time as the radiation of radiofrequency waves from the biopsy needle.

In such a case the frequency of radiofrequency waves may be set to approximately 450 kHz. The harmonic waves of the radiofrequency waves at that frequency may be overlapped with the frequency band of the ultrasonic waves to be transmitted and to be received by using the ultrasonic probe (approximately a few MHz) to cause some noises, which may appear on the ultrasonic image, resulting in the problem of the degradation of the image quality.

BRIEF DESCRIPTION OF THE INVENTION

It is desirable that the problem described previously is solved.

A first aspect of the invention provides an ultrasonic diagnosis apparatus including: an ultrasonic probe for transmitting and for receiving ultrasonic waves; an image generator unit for generating an ultrasonic image based on the echo signals received by the ultrasonic probe; and a display unit for displaying an ultrasonic image generated by the image generator unit, the ultrasonic diagnosis apparatus including: a display controller unit for displaying on the display unit, an ultrasonic image at the time of non-radiation of the radiofrequency waves generated based on the echo signals received by the ultrasonic probe at the time when the radiofrequency waves are not radiated from the radiofrequency wave cautery treatment device, in place of the ultrasonic image at the time of radiation of the radiofrequency waves generated based on the echo signals received by the ultrasonic probe at the time when the radiofrequency waves are radiated from a radiofrequency wave cautery treatment device having a biopsy needle for radiating radiofrequency waves.

A second aspect of the invention provides an ultrasonic diagnosis apparatus in accordance with the first aspect of the invention, in which the display controller unit, with respect to the ultrasonic image generated by the image generator unit, determines that the image is either an ultrasonic image at the time of radiation of the radiofrequency waves or an ultrasonic image at the time of non-radiation of the radiofrequency waves for each single frame, and displays the image on the display unit if the image is determined to be the ultrasonic image at the time of non-radiation of the radiofrequency waves, and displays on the display unit an ultrasonic image at the time of non-radiation of the radiofrequency waves in a frame prior to the image if the image is determined to be an ultrasonic image at the time of radiation of the radiofrequency waves.

A third aspect of the invention provides an ultrasonic diagnosis apparatus in accordance with the second aspect described above of the invention, in which the display controller unit determines that the ultrasonic image is an ultrasonic image at the time of radiation of the radiofrequency waves if the mean brightness of the region of interest in a B-mode image generated by the image generator unit is equal to or more than a predetermined value, or determines that the ultrasonic image is an ultrasonic image at the time of non-radiation of the radiofrequency waves if the value is less than the predetermined value.

A fourth aspect of the invention provides an ultrasonic diagnosis apparatus in accordance with the second aspect described above, in which the display controller unit determines that the image is an ultrasonic image at the time of radiation of the radiofrequency waves if the value of variance or the value of power in a Doppler image generated by the image generator unit is equal to or more than a predetermined value, or determines that the image is an ultrasonic image at the time of non-radiation of the radiofrequency waves if the value is less than the predetermined value.

A fifth aspect of the invention provides an ultrasonic diagnosis apparatus in accordance with the first aspect described above, in which the display controller unit displays an ultrasonic image on the display unit based on the information with respect to the radiation of radiofrequency waves which information is input from the radiofrequency wave cautery treatment device, and displays the ultrasonic image at the time of non-radiation of the radiofrequency waves in place of the ultrasonic image if an ultrasonic image is generated based on the echo signals received by the ultrasonic probe at the time of radiation of the radiofrequency waves.

A sixth aspect of the invention provides a radiofrequency wave cautery treatment device having a biopsy needle for radiating radiofrequency waves, in which the radiofrequency wave cautery treatment device outputs the information with respect to the radiation of the radiofrequency waves to the ultrasonic diagnosis apparatus in accordance with the fifth aspect described above of the invention.

A seventh aspect of the invention provides an ultrasonic diagnosis apparatus in accordance with the first aspect described above, which includes a permission signal generator unit for generating a radiofrequency wave permission signal for permitting the radiation of the radiofrequency waves from the radiofrequency wave cautery treatment device, outputting this radiofrequency wave radiation permission signal to the radiofrequency wave cautery treatment device to instruct to radiate the radiofrequency waves from the radiofrequency wave cautery treatment device, wherein the display controller unit displays on the display unit an ultrasonic image at the time of non-radiation of the radiofrequency waves generated based on the echo signals received by the ultrasonic probe at the time of non-outputting the radiofrequency wave radiation permission signal, in place of the ultrasonic image at the time of radiation of the radiofrequency waves generated based on the echo signals received by the ultrasonic probe at the time of outputting the radiofrequency wave radiation permission signal from the permission signal generator unit.

An eighth aspect of the invention provides a radiofrequency wave cautery treatment device having a biopsy needle for radiating radiofrequency waves, which includes: a generator unit of a radiofrequency wave radiation instruction signal for radiating the radiofrequency waves from the biopsy needle; and a radiofrequency wave radiation permission unit for outputting the radiofrequency wave radiation instruction signal to radiate the radiofrequency waves from the biopsy needle when the radiofrequency wave radiation instruction signal is input from the radiofrequency wave radiation instruction signal generator unit, and when the radiofrequency wave radiation permission signal is input from the permission signal generator unit in the ultrasonic diagnosis apparatus in accordance with the seventh aspect described above.

A ninth aspect of the invention provides an ultrasonic diagnosis and treatment system including: an ultrasonic probe for transmitting and for receiving ultrasonic waves; an image generator unit for generating an ultrasonic image based on the echo signals received by the ultrasonic probe; a display unit for displaying an ultrasonic image generated by the image generator unit; and a biopsy needle for radiating radiofrequency waves, the ultrasonic diagnosis and treatment system including: a display controller unit for displaying on the display unit an ultrasonic image at the time of non-radiation of the radiofrequency waves generated based on the echo signals received by the ultrasonic probe at the time when the radiofrequency waves are not radiated from the biopsy needle, in place of the ultrasonic image at the time of radiation of the radiofrequency waves generated based on the echo signals received by the biopsy needle at the time of radiating the radiofrequency wave from the biopsy needle.

A tenth aspect of the invention provides ultrasonic diagnosis and treatment system in accordance with the ninth aspect described above, which includes: an ultrasonic diagnosis apparatus having the ultrasonic probe, the image generator unit, the display unit, and the display controller unit; and a radiofrequency wave cautery treatment device having the biopsy needle.

An eleventh aspect of the invention provides an ultrasonic diagnosis and treatment system in accordance with the ninth or the tenth aspect described above, in which the display controller unit determines whether or not the ultrasonic image generated by the image generator unit is an ultrasonic image at the time of radiation of the radiofrequency wave or an ultrasonic image at the time of non-radiation of the radiofrequency wave for each single frame, and displays the ultrasonic image on the display unit if the image is determined to be an ultrasonic image at the time of non-radiation of the radiofrequency wave, and displays on the display unit an ultrasonic image at the time of non-radiation of the radiofrequency wave of the frame prior to the image if the ultrasonic image is determined to be an ultrasonic image at the time of radiation of the radiofrequency wave.

A twelfth aspect of the invention provides an ultrasonic diagnosis and treatment system in accordance with the eleventh aspect described above, in which the display controller unit determines that the ultrasonic image is an ultrasonic image at the time of radiation of the radiofrequency waves if the mean brightness of the region of interest in a B-mode image generated by the image generator unit is equal to or more than a predetermined value, or determines that the ultrasonic image is an ultrasonic image at the time of non-radiation of the radiofrequency waves if the value is less than the predetermined value.

A thirteenth aspect of the invention provides an ultrasonic diagnosis and treatment system in accordance with the eleventh aspect described above, in which the display controller unit determines that the image is an ultrasonic image at the time of radiation of the radiofrequency waves if the value of variance or the value of power in a Doppler image generated by the image generator unit is equal to or more than a predetermined value, or determines that the image is an ultrasonic image at the time of non-radiation of the radiofrequency waves if the value is less than the predetermined value.

A fourteenth aspect of the invention provides an ultrasonic diagnosis and treatment system in accordance with the tenth aspect described above, in which the display controller unit displays an ultrasonic image on the display unit based on the information with respect to the radiation of radiofrequency waves which information is input from the radiofrequency wave cautery treatment device, and displays, in place of the ultrasonic image, the ultrasonic image at the time of non-radiation of the radiofrequency waves if an ultrasonic image is generated based on the echo signals received by the ultrasonic probe at the time of radiation of the radiofrequency waves.

A fifteenth aspect of the invention provides an ultrasonic diagnosis and treatment system in accordance with the tenth aspect described above, in which: the ultrasonic diagnosis apparatus includes a permission signal generator unit for generating a radiofrequency wave permission signal for permitting the radiation of the radiofrequency waves from the radiofrequency wave cautery treatment device, outputting this radiofrequency wave radiation permission signal to the radiofrequency wave cautery treatment device to instruct to radiate the radiofrequency waves from the radiofrequency wave cautery treatment device; and the display controller unit displays on the display unit an ultrasonic image at the time of non-radiation of the radiofrequency waves generated based on the echo signals received by the ultrasonic probe at the time of non-outputting the radiofrequency wave radiation permission signal, in place of the ultrasonic image at the time of radiation of the radiofrequency waves generated based on the echo signals received by the ultrasonic probe at the time of outputting the radiofrequency wave radiation permission signal from the permission signal generator unit.

A sixteenth aspect of the invention provides an ultrasonic diagnosis and treatment system in accordance with the fifteenth aspect described above, wherein the radiofrequency wave cautery treatment device includes: a generator unit of a radiofrequency wave radiation instruction signal for radiating the radiofrequency waves from the biopsy needle; and a radiofrequency wave radiation permission unit for outputting the radiofrequency wave radiation instruction signal to radiate the radiofrequency waves from the biopsy needle when the radiofrequency wave radiation instruction signal is input from the radiofrequency wave radiation instruction signal generator unit, and when the radiofrequency wave radiation permission signal is input from the permission signal generator unit.

A seventeenth aspect of the invention provides an ultrasonic diagnosis and treatment apparatus, which includes a body of the apparatus having: an ultrasonic probe for transmitting and for receiving ultrasonic waves; and a biopsy needle for radiating radiofrequency waves connected thereto, the body of the apparatus including: an image generator unit for generating an ultrasonic image based on the echo signals received by the ultrasonic probe; and a display unit for displaying an ultrasonic image generated by the image generator unit, the body of the apparatus further including a display controller unit for displaying on the display unit an ultrasonic image at the time of non-radiation of the radiofrequency waves generated based on the echo signals received by the ultrasonic probe at the time when the radiofrequency waves are not radiated from the biopsy needle, in place of the ultrasonic image at the time of radiation of the radiofrequency waves generated based on the echo signals received by the biopsy needle at the time of radiating the radiofrequency wave from the biopsy needle.

An eighteenth aspect of the invention provides an ultrasonic diagnosis and treatment apparatus in accordance with the seventeenth aspect described above, in which the display controller unit determines whether or not the ultrasonic image generated by the image generator unit is an ultrasonic image at the time of radiation of the radiofrequency wave or an ultrasonic image at the time of non-radiation of the radiofrequency wave for each single frame, and displays the ultrasonic image on the display unit if the image is determined to be an ultrasonic image at the time of non-radiation of the radiofrequency wave, and displays on the display unit an ultrasonic image at the time of non-radiation of the radiofrequency wave of the frame prior to the image if the ultrasonic image is determined to be an ultrasonic image at the time of radiation of the radiofrequency wave.

A nineteenth aspect of the invention provides an ultrasonic diagnosis and treatment apparatus in accordance with the seventeenth aspect described above, in which apparatus the display controller unit displays an ultrasonic image on the display unit based on the information with respect to the radiation of radiofrequency waves, and displays, in place of the ultrasonic image, the ultrasonic image at the time of non-radiation of the radiofrequency waves if an ultrasonic image is generated based on the echo signals received by the ultrasonic probe at the time of radiation of the radiofrequency waves.

In accordance with the first and ninth aspects of the invention, as the display controller unit displays on the display unit the ultrasonic image at the time of non-radiation of the radiofrequency wave in place of the ultrasonic image at the time of radiation of the radiofrequency wave, the degradation of the image quality caused by the radiofrequency waves may be prevented for the ultrasonic image to be displayed on the display unit.

In accordance with the second and eleventh aspects of the invention, the ultrasonic image generated by the image generator unit is displayed on the display unit if the image is an ultrasonic image at the time of non-radiation of the radiofrequency wave. On the other hand, if the image is the ultrasonic image at the time of radiation of the radiofrequency wave, an ultrasonic image at the time of non-radiation of the radiofrequency wave of the previous frame of the radiation will be displayed on the display unit in place of the image. Therefore the degradation of the image quality of the ultrasonic image, which is caused by the radiofrequency wave, may be prevented for the ultrasonic image to be displayed on the display unit.

In accordance with the third and twelfth aspects of the invention, the determination of that the image is the ultrasonic image at the time of radiation of the radiofrequency wave or the ultrasonic image at the time of non-radiation of the radiofrequency wave may be performed based on the mean brightness in the region of interest of the B-mode image.

In accordance with the fourth and thirteenth aspects of the invention, the determination that the image is the ultrasonic image at the time of radiation of the radiofrequency wave or the ultrasonic image at the time of non-radiation of the radiofrequency wave may be performed based on the variance value or the power value of a Doppler image.

In accordance with the fifth and fourteenth aspects of the invention, as the display controller unit displays on the display unit an ultrasonic image based on the information with respect to the radiation of the radiofrequency wave, which information is input from the radiofrequency wave cautery treatment device, if at the time of radiation of the radiofrequency wave an ultrasonic image is generated based on the echo signals received by using the ultrasonic probe, the ultrasonic image at the time of non-radiation of the radiofrequency wave will be displayed in place of that image, so that the degradation of the image quality caused by the radiofrequency wave may be prevented.

In accordance with the sixth aspect of the invention, the information with respect to the radiation of the radiofrequency wave is output to the ultrasonic diagnosis apparatus in accordance with the fifth aspect of the invention, and based on the information, the ultrasonic image at the time of non-radiation of the radiofrequency wave is displayed in place of the ultrasonic image at the time of radiation of the radiofrequency wave by the display controller unit in the ultrasonic diagnosis apparatus.

In accordance with the seventh and fifteenth aspects of the invention, in place of the ultrasonic image at the time of radiation of the radiofrequency wave which is generated based on the echo signal received by the ultrasonic probe at the time when the permission signal generator unit outputs the radiofrequency wave radiation permission signal to radiate the radiofrequency wave from the radiofrequency wave cautery treatment device, the ultrasonic image at the time of non-radiation of the radiofrequency wave which is generated based on the echo signals received by the ultrasonic probe at the time of non-radiation of the radiofrequency wave, namely at the time of non-output of the radiofrequency wave radiation permission signal, so that the degradation of the image quality caused by the radiofrequency wave may be prevented for the ultrasonic image to be displayed on the display unit.

In accordance with the eighth aspect of the invention, the radiofrequency wave radiation permission unit outputs the radiofrequency wave radiation instruction signal to permit to radiate radiofrequency waves from the biopsy needle only when the radiofrequency wave radiation instruction signal is input thereto and if the radiofrequency wave radiation permission signal is also input thereto. Then the ultrasonic diagnosis apparatus displays on the display unit, in place of the ultrasonic image at the time of radiation of the radiofrequency wave, which is generated based on the echo signals received by the ultrasonic probe at the time of outputting the radiofrequency wave radiation permission signal from the permission signal generator unit, namely at the time of radiating the radiofrequency wave, the ultrasonic image at the time of non radiating the radiofrequency wave, which is generated based on the echo signals received by the ultrasonic probe at the time of non-outputting the radiofrequency wave radiation permission signal, namely at the time of non radiating the radiofrequency wave. Thereby for the ultrasonic image to be displayed on the display unit, the degradation of the image quality caused by the radiofrequency waves may be prevented.

In accordance with the tenth aspect of the invention, in an ultrasonic diagnosis and treatment system including an ultrasonic diagnosis apparatus having the ultrasonic probe, the image generator unit, the display unit, and the display controller unit, and a radiofrequency wave cautery treatment device having the biopsy needle, the degradation of the image quality caused by the radiofrequency wave may be prevented for the ultrasonic image to be displayed on the display unit.

In accordance with the sixteenth aspect of the invention, the radiofrequency wave radiation permission unit outputs the radiofrequency wave radiation instruction signal to instruct to radiate the radiofrequency wave from the biopsy needle only when the radiofrequency wave radiation instruction signal is input thereto and if the radiofrequency wave radiation permission signal is also input thereto. Then the ultrasonic image at the time of non-radiation of the radiofrequency wave, which is generated based on the echo signals received by the ultrasonic probe at the time of non-outputting the radiofrequency wave radiation permission signal, namely at the time of non radiating the radiofrequency wave, will be displayed on the display unit, in place of the ultrasonic image at the time of radiation of the radiofrequency wave which is generated based on the echo signals received by the ultrasonic probe at the time of outputting the radiofrequency wave radiation permission signal, namely at the time of radiating the radiofrequency wave. For the ultrasonic image to be displayed on the display unit, the degradation of the image quality caused by the radiofrequency wave may be thereby prevented.

In accordance with the seventeenth aspect of the invention, the ultrasonic diagnosis and treatment apparatus having the advantage in accordance with the first and ninth aspects of the invention may be obtained, and the control associating the control of the generation of ultrasonic images and the radiation control of the radiofrequency wave may be achieved with a simple configuration because the function for generating the ultrasonic image by transmitting and receiving the ultrasonic waves and the function for performing the cautery treatment by radiating the radiofrequency waves are integratedly combined in one apparatus.

In accordance with the eighteenth aspect of the invention, the ultrasonic image generated by the image generator unit will be displayed on the display unit if the image is the ultrasonic image at the time of non-radiation of the radiofrequency wave. On the other hand, if the image is the ultrasonic image at the time of radiation of the radiofrequency wave, the ultrasonic image at the time of non-radiation of the radiofrequency wave, of a prior frame, in place of the image in concern, will be displayed. Therefore for the ultrasonic image to be displayed on the display unit, the degradation of the image quality of the ultrasonic image, which is caused by the radiofrequency wave, may be prevented.

In accordance with the nineteenth aspect of the invention, an ultrasonic image will be displayed on the display unit by the display controller unit based on the information with respect to the radiation of the radiofrequency wave, and if the ultrasonic image is generated based on the echo signals received by the ultrasonic probe at the time of radiating the radiofrequency wave, the ultrasonic image at the time of non-radiation of the radiofrequency wave will be displayed in place of the image generated, so that the degradation of the image quality caused by the radiofrequency wave may be prevented for the ultrasonic image to be displayed on the display unit.

Further objects and advantages of the present invention will be apparent from the following description of the preferred embodiments of the invention as illustrated in the accompanying drawings.

DETAILED DESCRIPTION OF THE INVENTION

Various embodiments of the invention will be described in greater details herein below with reference to the accompanying drawings.

Firstly, a first embodiment of the invention will be described in greater details. Now referring to FIG. 1 there is shown a schematic block diagram illustrating the configuration of an ultrasonic diagnosis apparatus in accordance with the first embodiment.

Figure 1:
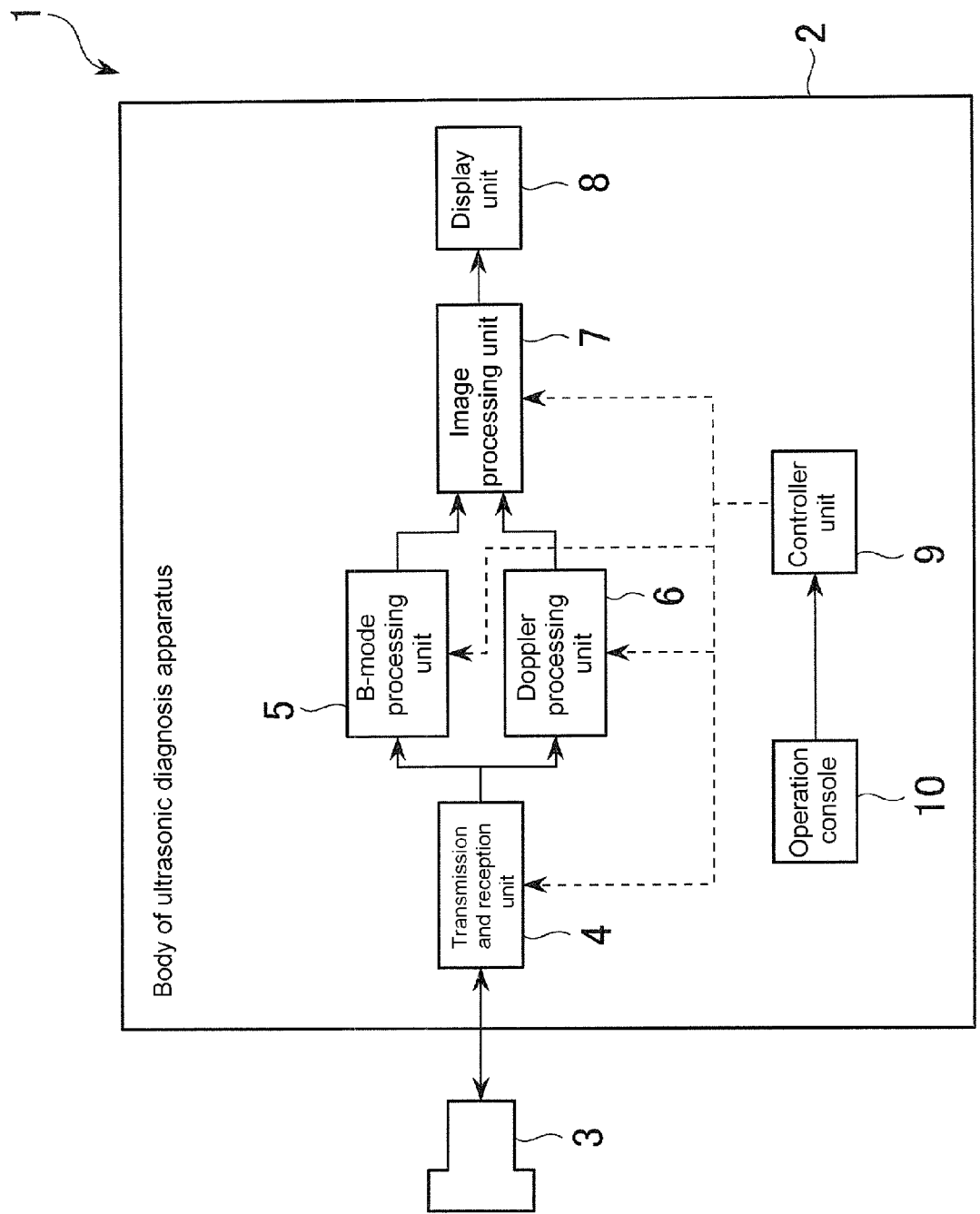
FIG. 1 is a schematic block diagram illustrating the configuration of an ultrasonic diagnosis apparatus in accordance with a first embodiment.

The ultrasonic diagnosis apparatus 1 as shown in FIG. 1 is configured by having a body of the ultrasonic diagnosis apparatus 2, and an ultrasonic probe 3 connected to the body of the ultrasonic diagnosis apparatus 2. The ultrasonic probe 3 has an array of a plurality of ultrasonic transducers, not shown in the figure. Each of the ultrasonic wave transducers may be made of a piezoelectric material such as the PZT ceramics (lead zirconate titanate).

To the ultrasonic probe 3, a biopsy needle (not shown in the figure) for radiating radiofrequency waves is attached via a biopsy adapter (not shown in the figure).

The body of the ultrasonic diagnosis apparatus 2 has a transmission and reception unit 4, a B-mode processing unit 5, a Doppler processing unit 6, and an image processing unit 7, a display unit 8, a controller unit 9, and an operation console 10. The ultrasonic probe 3 is connected to the transmission and reception unit 4.

Figure 2:
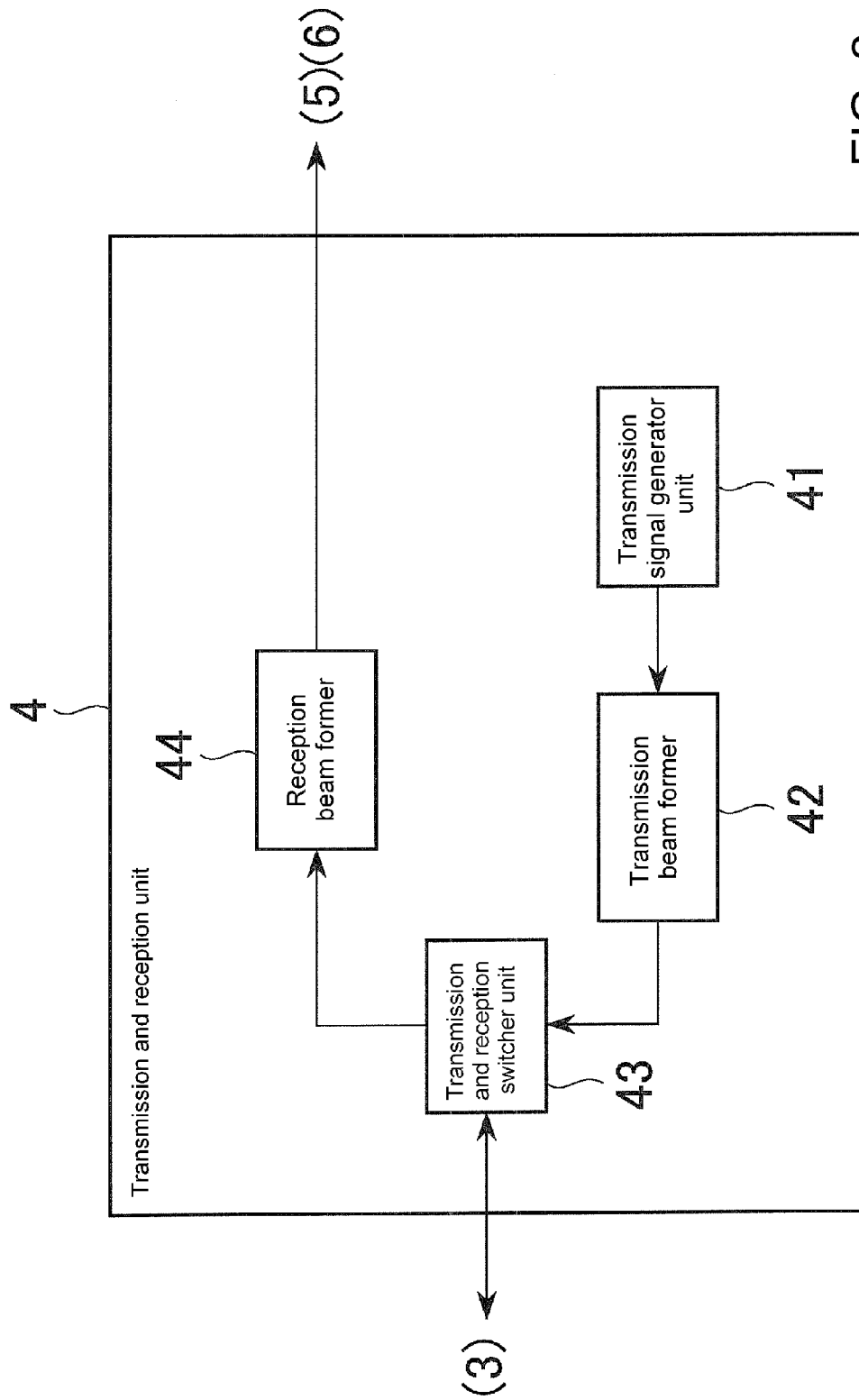
FIG. 2 is a schematic block diagram illustrating the configuration of the transmission and reception unit shown in FIG. 1.

The transmission and reception unit 4 will be described with reference to FIG. 2. The transmission and reception unit 4 has a transmission signal generator unit 41, a transmission beam former 42, a transmission and reception switcher unit 43, and a reception beam former 44.

The transmission signal generator unit 41 is for periodically generating the transmission signals and inputting them to the transmission beam former 42. The cycle of the transmission signal is controlled by the controller unit 9.

The transmission beam former 42 is for beam forming of the transmitted ultrasonic waves, which beam former generates the transmission beam forming signals for forming the ultrasonic wave beam in a predetermined direction. The beam forming signal is composed of a plurality of driving signals with the difference of timing added in correspondence with the direction. The beam forming is controlled by the controller unit 9. The transmission beam former 42 outputs the transmission beam forming signals to the transmission and reception switcher unit 43.

The transmission and reception switcher unit 43 outputs the transmission beam forming signal to the array of ultrasonic transducers. In the array of ultrasonic transducers, a plurality of ultrasonic transducers that constitute a transmission aperture each generates the ultrasonic waves having a difference of phase in correspondence with the difference of timing in the driving signals. The wave front synthesis of the ultrasonic waves will form the ultrasonic beam along the acoustic ray in the predetermined direction.

To the transmission and reception switcher unit 43 the reception beam former 44 is connected. The transmission and reception switcher unit 43 outputs to the reception beam former 44 a plurality of echo signals received by the reception aperture within the array of ultrasonic transducers.

The reception beam former 44 is for beam forming of the received ultrasonic waves in correspondence with the acoustic array of the transmitted ultrasonic waves, which beam former adjusts the phase by adding the difference of timing to a plurality of received ultrasonic echoes, then adding them to generate an echo signal along the acoustic ray in the predetermined direction. The beam forming of the received ultrasonic waves is controlled by the controller unit 9.

The transmission and reception unit 4 is connected to the B-mode processing unit 5 and to the Doppler processing unit 6. The echo signals for each acoustic ray to be output from the transmission and reception unit 4 will be input to the B-mode processing unit 5 and to the Doppler processing unit 6.

Figure 3:
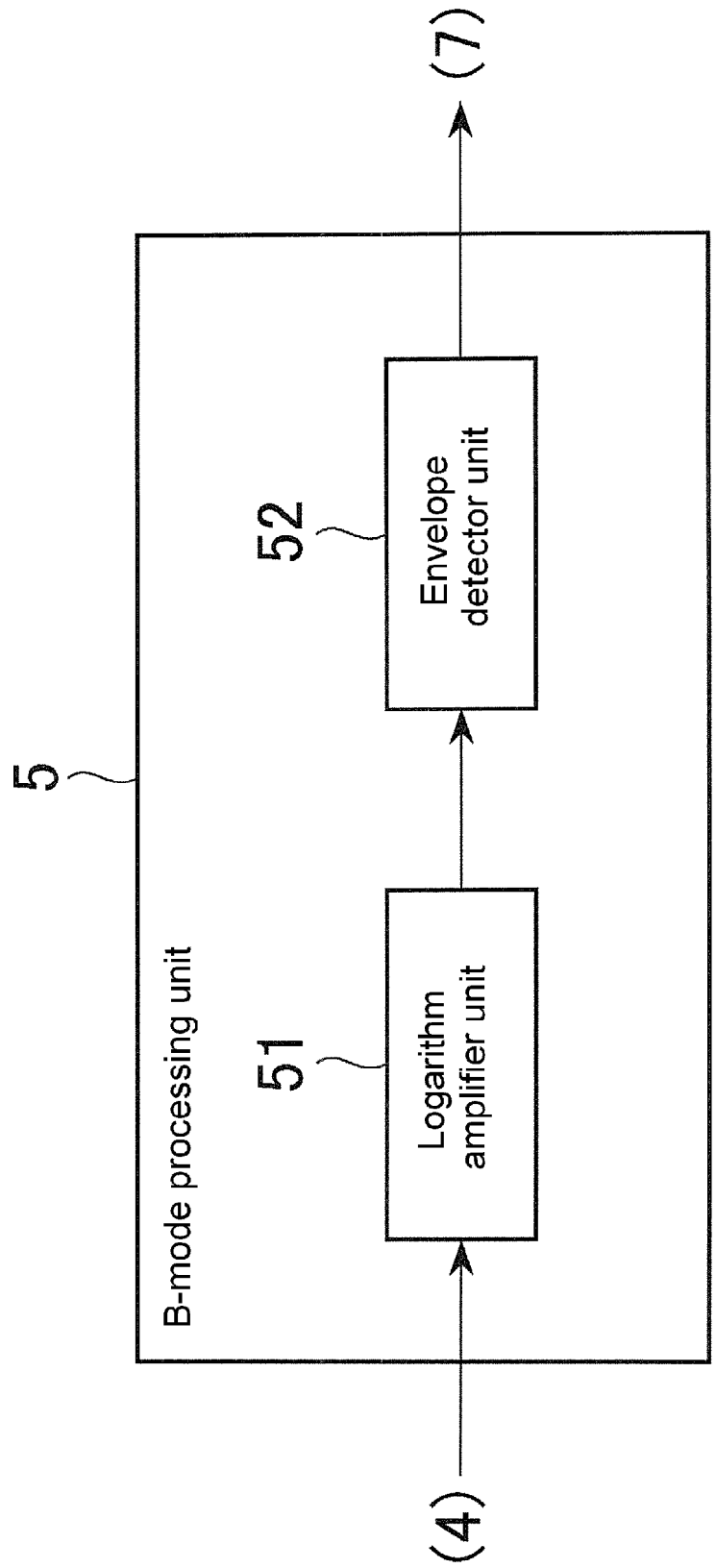
FIG. 3 is a schematic block diagram illustrating the configuration of the B-mode processing unit shown in FIG. 1.

The B-mode processing unit 5 is for generating B-mode image data for each acoustic ray based on the echo signals. Now referring to FIG. 3 there is shown a schematic block diagram illustrating the configuration of the B-mode processing unit 5. The B-mode processing unit 5 shown in FIG. 3 has a logarithm amplifier unit 51, and an envelope detector unit 52.

The B-mode processing unit 5 performs the logarithm amplification of the echo signals in the logarithm amplifier unit 51, then performs the envelope detection in the envelope detector unit 52, in order to obtain the signal indicative of the intensity of echoes at each of the reflection points on the acoustic ray, namely the A scope signal, thereafter the amplitude of each instance on the A scope signal is used as the brightness value to generate B-mode image data.

The Doppler processing unit 6 is for generating Doppler image data for each acoustic ray based on the echo signals. The Doppler image data includes the flow velocity data, the variance data, and the power data as will be described in greater details later.

Figure 4:
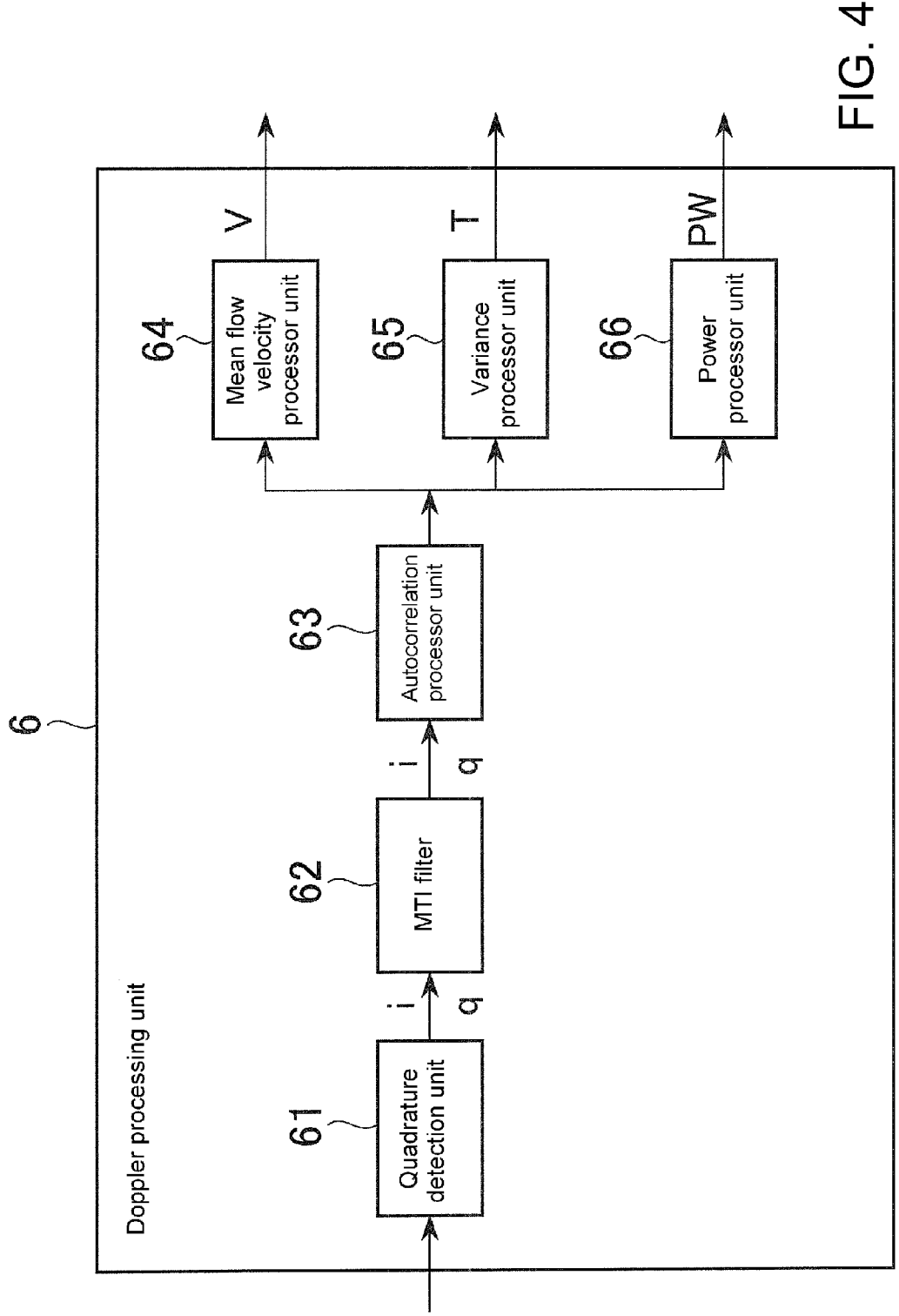
FIG. 4 is a schematic block diagram illustrating the configuration of the Doppler mode processing unit shown in FIG. 1.

Now referring to FIG. 4 there is shown a schematic block diagram illustrating the configuration of the Doppler processing unit 6. As is shown in FIG. 4, the Doppler processing unit 6 includes a quadrature detection unit 61, an MTI (moving target indication) filter 62, an autocorrelation processor unit 63, a mean flow velocity processor unit 64, a variance processor unit 65, and a power processor unit 66.

The Doppler processing unit 6 performs the quadrature detection of the echo signals in the quadrature detection unit 61, then MTI processing in the MTI filter 62 to determine the amount of Doppler shift of the echo signals. Also it performs in the autocorrelation processor unit 63 the autocorrelation processing with respect to the output signal from the MTI filter 62. Then the mean flow velocity processor unit 64 determines the mean flow velocity V from the result of the autocorrelation processing, the variance processor unit 65 determines the variance T of the flow from the result of the autocorrelation processing, then the power processor unit 66 determines the power PW of the Doppler signal from the result of the autocorrelation processing. The mean flow velocity will be referred to as simply the flow velocity herein below. The variance of the flow velocity will also be referred to as simply the variance, and the power of the Doppler signal will be referred to as simply the power, herein below.

The Doppler processing unit 6 will obtain the data indicative of respectively the flow velocity V, the variance T, and the power PW of the echo source that is moving within the subject for each acoustic ray. These items of data indicate the flow velocity, the variance, and the power of the pixel on the acoustic ray. It should be noted here that the flow velocity may be obtained as the components in the direction of the acoustic ray. Also it should be noted that the direction reaching to the ultrasonic probe 3 and the direction separated away therefrom are distinguished.

The B-mode processing unit 5 and the Doppler processing unit 6 are connected to the image processing unit 7. The image processing unit 7 generates a B-mode image and a Doppler image based on the data input from the B-mode processing unit 5 and from the Doppler processing unit 6, respectively. The B-mode processing unit 5, the Doppler processing unit 6, and the image processing unit 7 are an example of the preferred embodiment of the image generator unit in accordance with the invention.

Figure 5:
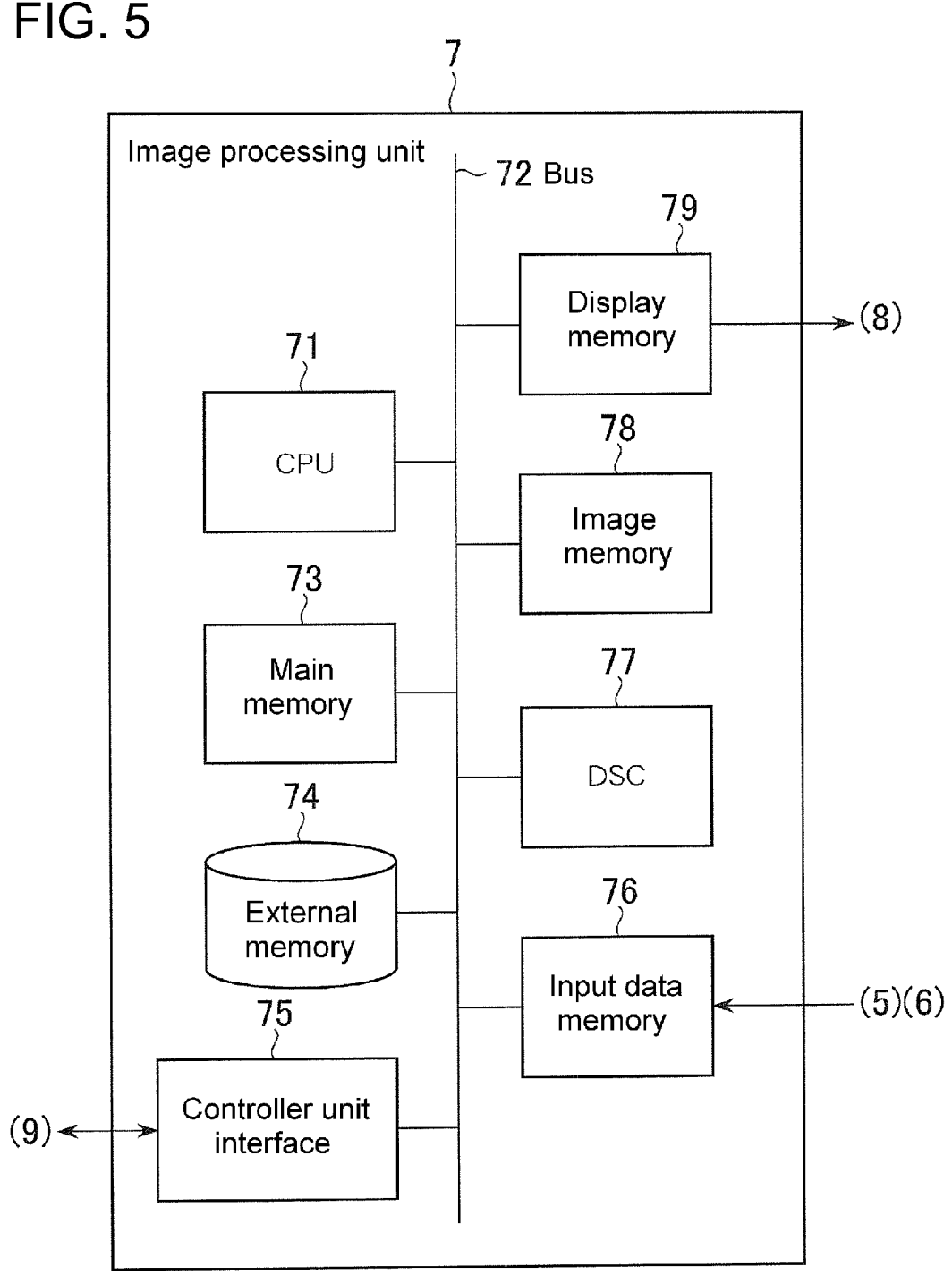
FIG. 5 is a schematic block diagram illustrating the configuration of the image processing unit shown in FIG. 1.

The image processing unit 7 will be described in greater details with reference to FIG. 5. FIG. 5 shows a block diagram illustrating an example of the configuration of the image processing unit 7. As shown in FIG. 5, the image processing unit 7 includes a CPU (central processing unit) 71. The CPU 71 is connected through a bus 72 to a main memory 73, an external memory 74, a controller unit interface 75, an input data memory 76, a digital scan converter (DSC) 77, an image memory 78, and a display memory 79.

The external memory 74 stores a program to be executed by the CPU 71. The external memory 74 also stores a variety of data used when the CPU 71 executes the program.

The CPU 71 loads and executes the program from the external memory 74 to the main memory 73 to perform a predetermined image processing. The CPU 71 transmits and receives control signals to and from the controller unit 9 through the controller unit interface 75 during the program execution.

The B-mode image data and the Doppler image data, which are input for each acoustic ray from the B-mode processing unit 5 and from the Doppler processing unit 6 respectively, are stored respectively in the input data memory 76. The data in the input data memory 76 will be scan converted by the DSC 77 to store in the image memory 78. The data in the image memory 78 will be output through the display memory 79 to the display unit 8. On the display unit 8, an ultrasonic image comprised of the B-mode image and the Doppler image will be displayed.

The CPU 71 displays on the display unit 8 the ultrasonic image to be generated based on the echo signals received by the ultrasonic probe at the time when the radiofrequency waves are not radiated from the radiofrequency wave cautery treatment device (not shown in the figure), namely the ultrasonic image at the time of non-radiation of the radiofrequency wave, in place of the ultrasonic image to be generated based on the echo signals received by the ultrasonic probe 3 at the time when the radiofrequency wave is radiated from the radiofrequency wave cautery treatment device, namely, the ultrasonic image at the time of radiation of the radiofrequency wave, and is an example of the preferred embodiment of the display controller unit in accordance with the invention.

More specifically, the CPU 71 determines for each single frame that it is an ultrasonic image at the time of radiation of the radiofrequency wave or an ultrasonic image at the time of non-radiation of the radiofrequency wave, for the data stored in the image memory 78, namely the ultrasonic image generated by the image generator unit. If the image is determined to be the ultrasonic image at the time of non-radiation of the radiofrequency wave, the image will be displayed on the display unit 8, or if the image is determined to be the ultrasonic image at the time of radiation of the radiofrequency wave then an ultrasonic image at the time of non-radiation of the radiofrequency wave of a previous frame which is prior to the image in question and stored in the image memory 78 is displayed on the display unit 8. The more specific determination method that the image is the ultrasonic image at the time of radiation of the radiofrequency wave or the ultrasonic image at the time of non-radiation of the radiofrequency wave will be described in greater details later.

To the image processing unit 7 the display unit 8 is connected. The display unit 8 is provided with the image signals from the image processing unit 7, and displays an ultrasonic image based thereon. The display unit 8 may be composed of a CRT or a liquid crystal display, which is capable of displaying color images.

To the transmission and reception unit 4, the B-mode processing unit 5, the Doppler processing unit 6, the image processing unit 7, and the display unit 8 as have been described above, the controller unit 9 is connected, and a variety of signals from the controller unit 9 is provided thereto. The B-mode operation and the Doppler mode operation will be conducted under the control of the controller unit 9.

To the controller unit 9 the operation console 10 is connected. The operation console 10 is operated by the operator, for input any appropriate instructions and information to the controller unit 9. The operation console 10 includes for example a keyboard or a pointing device as well as any other operating device.

Figure 6:
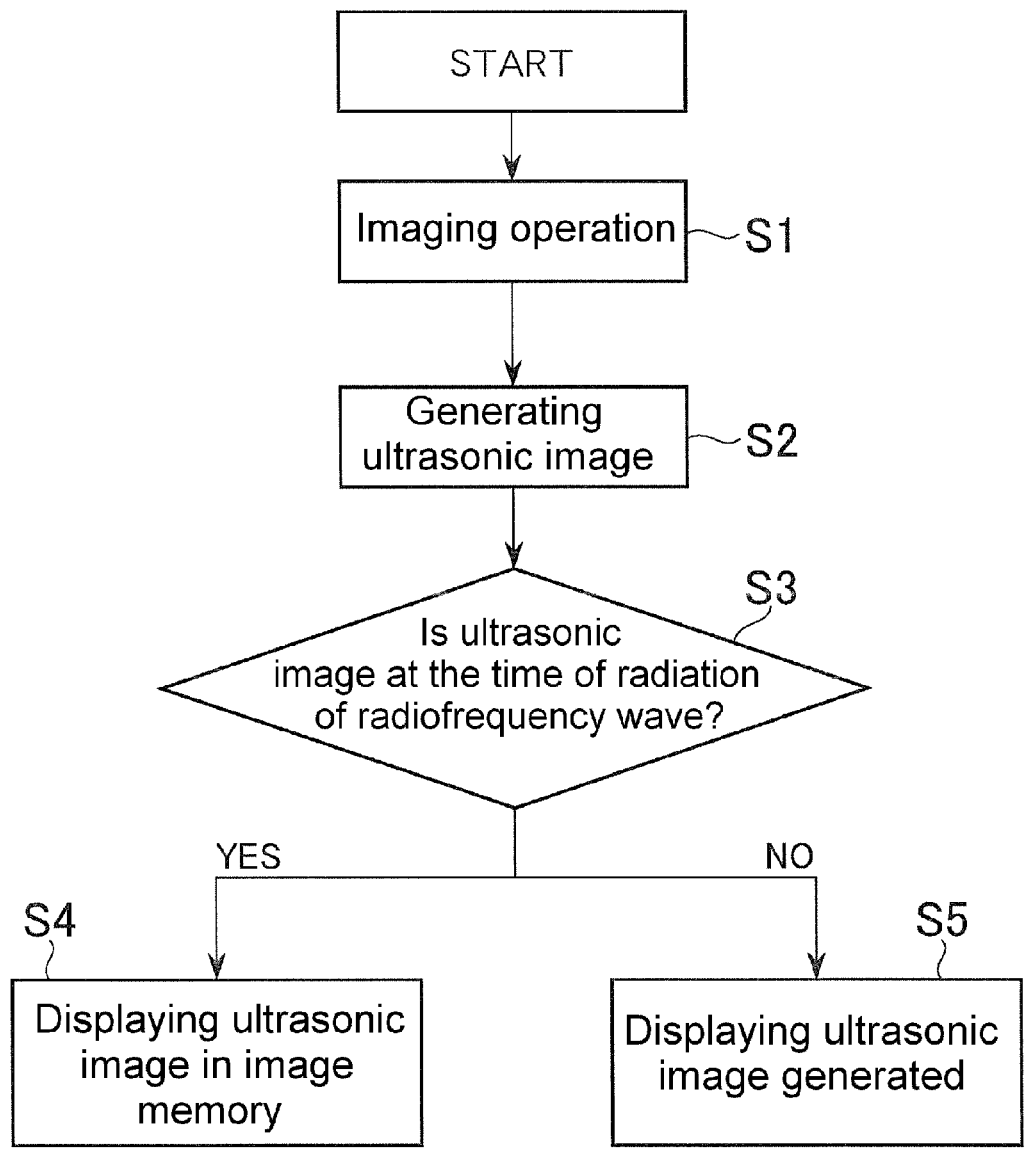
FIG. 6 is a flow chart illustrating an example of the operation of an ultrasonic diagnosis apparatus in accordance with the first embodiment.

Now the operation of the ultrasonic diagnosis apparatus 1 will be described in greater details with reference to FIG. 6. The ultrasonic diagnosis apparatus 1, in order to perform a cautery treatment by inserting the biopsy needle while viewing an ultrasonic image, in step S1, receives the echo signals by using the ultrasonic probe 3 by performing the imaging operation, then in step S2, generates an ultrasonic image based on the obtained echo signals. Then in step S3 the CPU 71 determines whether or not the image is the ultrasonic image at the time of radiation of the radiofrequency wave, for the obtained ultrasonic image. In step S3 if the obtained ultrasonic image is determined to be an ultrasonic image at the time of radiation of the radiofrequency wave then the process proceeds to step S4, and in step S4 the CPU 71 displays on the display unit 8 the ultrasonic image at the time of non-radiation of the radiofrequency wave which image is stored in the image memory 78. On the other hand in step S3 if the image is determined not to be the ultrasonic image at the time of radiation of the radiofrequency wave, namely the image is determined to be the ultrasonic image at the time of non-radiation of the radiofrequency wave, then the CPU 71 displays the image on the display unit 8 in step S5.

The steps S1 to S4 as have been described above will be described in greater details now. First, the step S1 will be described, and in step S1 the imaging operation is conducted for example using both the B-mode and the Doppler mode, by placing the ultrasonic probe 3 in contact with the subject then by operating the operation console 10. By doing this the B-mode imaging and the Doppler mode imaging are performed in the time sharing basis under the control of the controller unit 9. More specifically, one B-mode scan is performed every time a predetermined number of times of Doppler mode scans is performed, to thereby perform a mix scans of the B-mode and the Doppler mode.

In the B-mode, the transmission and reception unit 4 scans the inside of the subject in the sequential order of the acoustic rays through the ultrasonic probe 3 to receive sequentially the echo thereof. Also in the Doppler mode, the transmission and reception unit 4 scans the inside of the subject in the sequential order of the acoustic rays through the ultrasonic probe 3 to receive the echo thereof. At that time a plurality of numbers of the transmission of ultrasonic waves and of the reception of the echoes may be performed for each single acoustic ray.

Next, the step S2 will be described. The B-mode processing unit 5 will form the B-mode image data for each acoustic ray based on the echo signals to be input form the transmission and reception unit 4. The image processing unit 7 will store into the input data memory 76 the B-mode image data for each single acoustic ray to be input from the B-mode processing unit 5. By doing this an acoustic ray data space with respect to the B-mode image data is formed in the input data memory 76.

In addition, the Doppler processing unit 6 determines the flow velocity V, the variance T, and the power PW based on the echo signals. These calculation values will become the data indicating the velocity, the variance, and the power of the echo source, for each pixel and for each acoustic ray.

The image processing unit 7 stores in the input data memory 76 each Doppler image data for each acoustic ray and for each pixel, which is to be input from the Doppler processing unit 6. By doing this an acoustic ray data space with respect to each Doppler image data is formed within the input data memory 76.

The CPU 71 will scan and convert the B-mode image data and each Doppler image data in the input data memory 76 with the digital scan converter 77 to write down data into the image memory 78. At this time, the Doppler image data will be written thereto as the flow velocity distribution image data by combining the flow velocity V and the variance T, the power Doppler image data by using the power PW, or the power Doppler image data with the variance by combining the power PW and the variance T, and the variance image data by using the variance T.

The CPU 71 will write the B-mode image data and each Doppler image data to a different area in the image memory 78. Then the CPU 71, in part of the processing in the step S3, determines whether or not the B-mode image data or the Doppler image data written into the image memory 78 is the data of the ultrasonic image at the time of radiation of the radiofrequency wave.

For the B-mode image data, the determination method of whether or not the data is of the ultrasonic image at the time of radiation of the radiofrequency wave, for example, may be such that the operator operates the operation console 10 so as to set the region of interest for the B-mode image, then the determination is done whether the mean brightness of the B-mode image data within the region of interest is more than a predetermined value or not. In such a situation the predetermined value is the brightness when noises caused by the radiofrequency wave appear on the image. The mean brightness increases if the noises caused by the radiofrequency wave appear on the image, as compared with an image without the noises. Therefore, the CPU 71 may determine that the data is of the ultrasonic image at the time of radiation of the radiofrequency wave if the mean brightness within the region of interest in the B-mode image is equal to or more than the predetermined value, and the CPU may determine that the data is of the ultrasonic image at the time of non-radiation of the radiofrequency wave if the value is less than the predetermined value.

For the predetermined value, a numerical number may be input from the operation console 10 by the operator, or the mean brightness within the region of interest in the ultrasonic image at the time of non-radiation of the radiofrequency wave that is stored in the image memory 78 may be used.

The determination method of whether the Doppler image data is of the data of the ultrasonic image at the time of radiation of the radiofrequency wave, for example, may be such that the determination is made on whether or not the variance T is equal to or more than the predetermined value, or whether or not the power PW is equal to or more than the predetermined value. Here the predetermined value is the value of variance or the value of power when the noises caused by the radiofrequency wave appear on the image. When the noises caused by the radiofrequency wave appear on the image, the variance T and the power PW increase as compared with the case of no noise. Therefore, the CPU 71 will determine to be the data of the ultrasonic image at the time of radiation of the radiofrequency wave if the variance T or the power PW is equal to or more than the predetermined value, and will determine that the data is of the ultrasonic image at the time of non-radiation of the radiofrequency wave if the value is less than the predetermined value.

If the CPU 71 determines that at least one of either the obtained B-mode image data or the Doppler image data is of the data of the ultrasonic image at the time of radiation of the radiofrequency wave, then the process proceeds to step S4, where the CPU 71 displays on the display unit 8 the ultrasonic image at the time of non-radiation of the radiofrequency wave of a previous frame which is prior to the image. The displayed ultrasonic image at the time of non-radiation of the radiofrequency wave is an image stored in the image memory 78. On the other hand, if the CPU 71 determines that at least one of either the obtained B-mode image data or the Doppler image data is of the data of the ultrasonic image at the time of non-radiation of the radiofrequency wave, then the CPU 71 displays the image based on the data on the display unit 8 in the process of step S5.

The B-mode image to be displayed on the display unit 8 indicates a tomographic image of the tissue inside the body at the scan plane of the acoustic ray. Among the color Doppler images to be displayed on the display unit 8, the flow velocity distribution image is the image indicative of the two dimensional distribution of the flow velocity of the echo source. In this image, the display color differs in correspondence with the direction of the flow, and the brightness of the display color differs in correspondence with the flow velocity, as well as the purity of the display color varies by increasing the amount of color mixture of a predetermined color in correspondence with the variance.

The power Doppler image of the color Doppler images is the image indicative of the two dimensional distribution of the power of the Doppler signals. This image indicates the location of the moving echo source. Then the brightness of the display color of the image corresponds to the power. When this is combined with the variance, the purity of the display color varies by increasing the amount of the color mixture of a predetermined color in correspondence with the variance. The variance image is the image indicative of the two dimensional image of the variance values. This image also indicates the location of the moving echo source. The brightness of the display color corresponds to the amount of the variance.

When displaying the image as described above onto the display unit 8, the image will be synthesized with the B-mode image in the display memory 79, then the synthetic image will be displayed on the display unit 8 so that a color Doppler image may be presented in which the positional relationship of the tissues within the body is clearly depicted.

On the display unit 8 the ultrasonic images are displayed in real time basis by iteratively repeating the steps S1 to S4 or S5 as have been described above. Preferably, the radiation of the radiofrequency wave from the biopsy needle (not shown in the figure) attached to the radiofrequency wave cautery treatment device is intermittently performed so as not to degrade the real time property of the ultrasonic images.

In accordance with the ultrasonic diagnosis apparatus 1 as have been described above, if the ultrasonic image to be generated is the ultrasonic image at the time of radiation of the radiofrequency wave, then an ultrasonic image at the time of non-radiation of the radiofrequency wave which is in a previous frame prior to the image will be displayed on the display unit 8, so that the ultrasonic image at the time of non-radiation of the radiofrequency wave can be displayed in place of the ultrasonic image at the time of radiation of the radiofrequency wave. Therefore for the ultrasonic image to be displayed on the display unit 8, the degradation of the image quality of the ultrasonic image that is caused by the radiofrequency wave may be prevented.

Next, a second embodiment of the invention will be described in greater details herein below. Now referring to FIG. 7 there is shown a schematic block diagram illustrating the configuration of an ultrasonic diagnosis and treatment system in accordance with the second embodiment.

Figure 7:
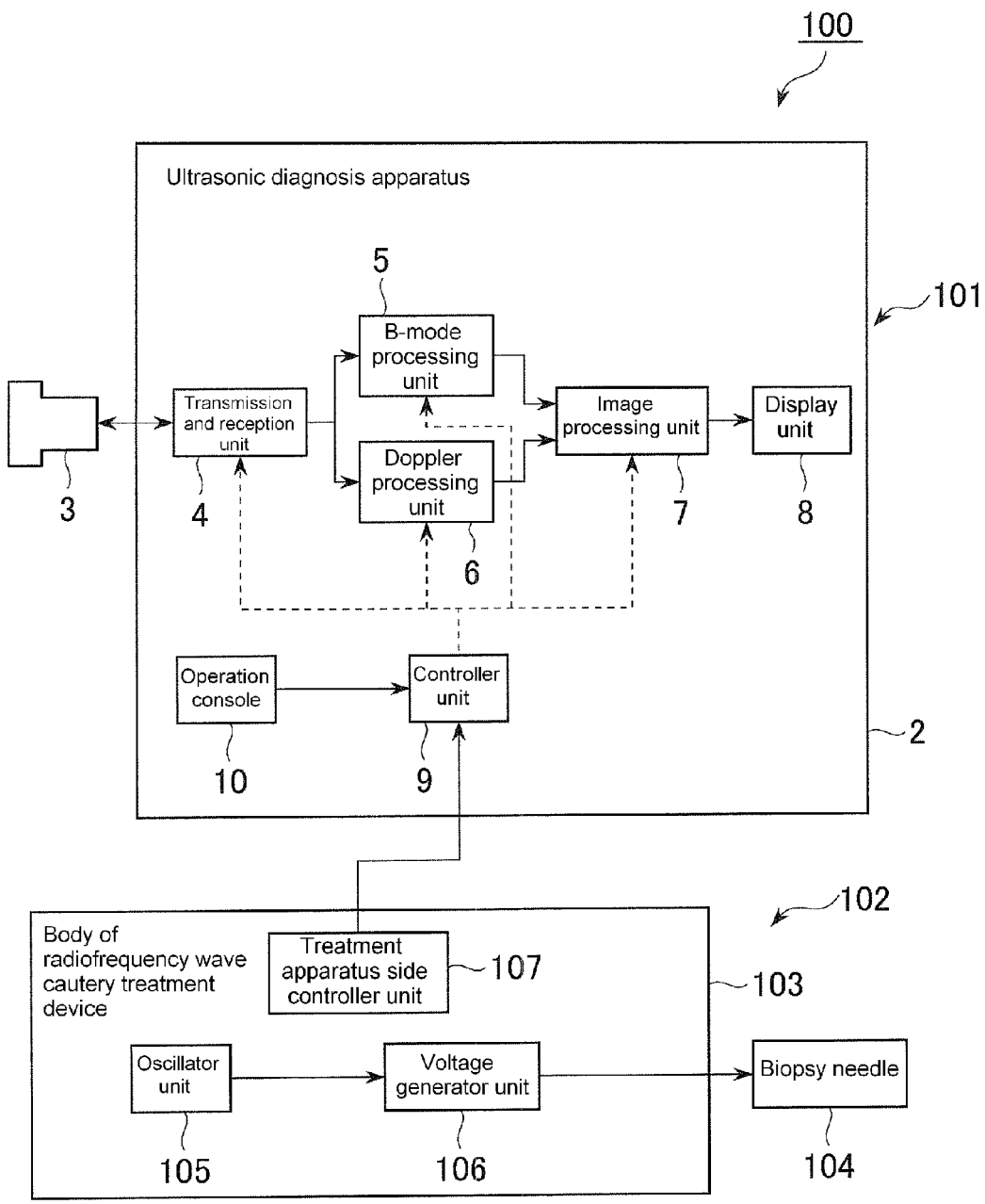
FIG. 7 is a schematic block diagram illustrating the configuration of an ultrasonic diagnosis and treatment system in accordance with a second embodiment.

The ultrasonic diagnosis and treatment system 100 as shown in FIG. 7 includes an ultrasonic diagnosis apparatus 101 and a radiofrequency wave cautery treatment device 102. The ultrasonic diagnosis apparatus 101 is as similar to the ultrasonic diagnosis apparatus 1 in the previous first embodiment, and is comprised of the body of the ultrasonic diagnosis apparatus 2 and the ultrasonic probe 3. The radiofrequency wave cautery treatment device 102 is comprised of a body of the radiofrequency wave cautery treatment device 103 and a biopsy needle 104 connected to the body of the radiofrequency wave cautery treatment device 103.

In this embodiment, the controller unit 9 in the body of the ultrasonic diagnosis apparatus 2 displays an ultrasonic image on the display unit 8 based on the information with respect to the radiation of the radiofrequency wave to be input from the radiofrequency wave cautery treatment device 102. The details will be described in greater details later.

The body of the radiofrequency wave cautery treatment device 103 includes an oscillator unit 105, a voltage generator unit 106, and a treatment apparatus side controller unit 107. The radiation pulses of the radiofrequency wave for radiating the radiofrequency wave from the biopsy needle 104 is output from the oscillator unit 105. The radiofrequency wave radiation instruction pulses from the oscillator unit 105 will be output when the control signals from the treatment apparatus side controller unit 107 is input to the oscillator unit 105 by turning on the cautery switch (not shown in the figure) provided on the body of the radiofrequency wave cautery treatment device 103. The voltage generator unit 106 applies a voltage to the biopsy needle 104 when the radiofrequency wave radiation pulses are input. By doing this the radiofrequency wave will be radiated from the biopsy needle 104.

The biopsy needle 104 is attached to the ultrasonic probe 3 via a biopsy adapter (not shown in the figure).

The treatment apparatus side controller unit 107 outputs the radiofrequency wave radiation signals indicating that the radiofrequency wave is being radiated through the controller unit 9 to the CPU 71 in the image processing unit 7 of the body of the ultrasonic diagnosis apparatus 2, when the radiofrequency wave radiation pulses is output from the oscillator unit 105 and the radiofrequency wave is radiated from the biopsy needle 104. The radiofrequency wave radiation signal is an example of the preferred embodiment of the information with respect to the radiofrequency wave radiation in accordance with the invention.

Figure 8:
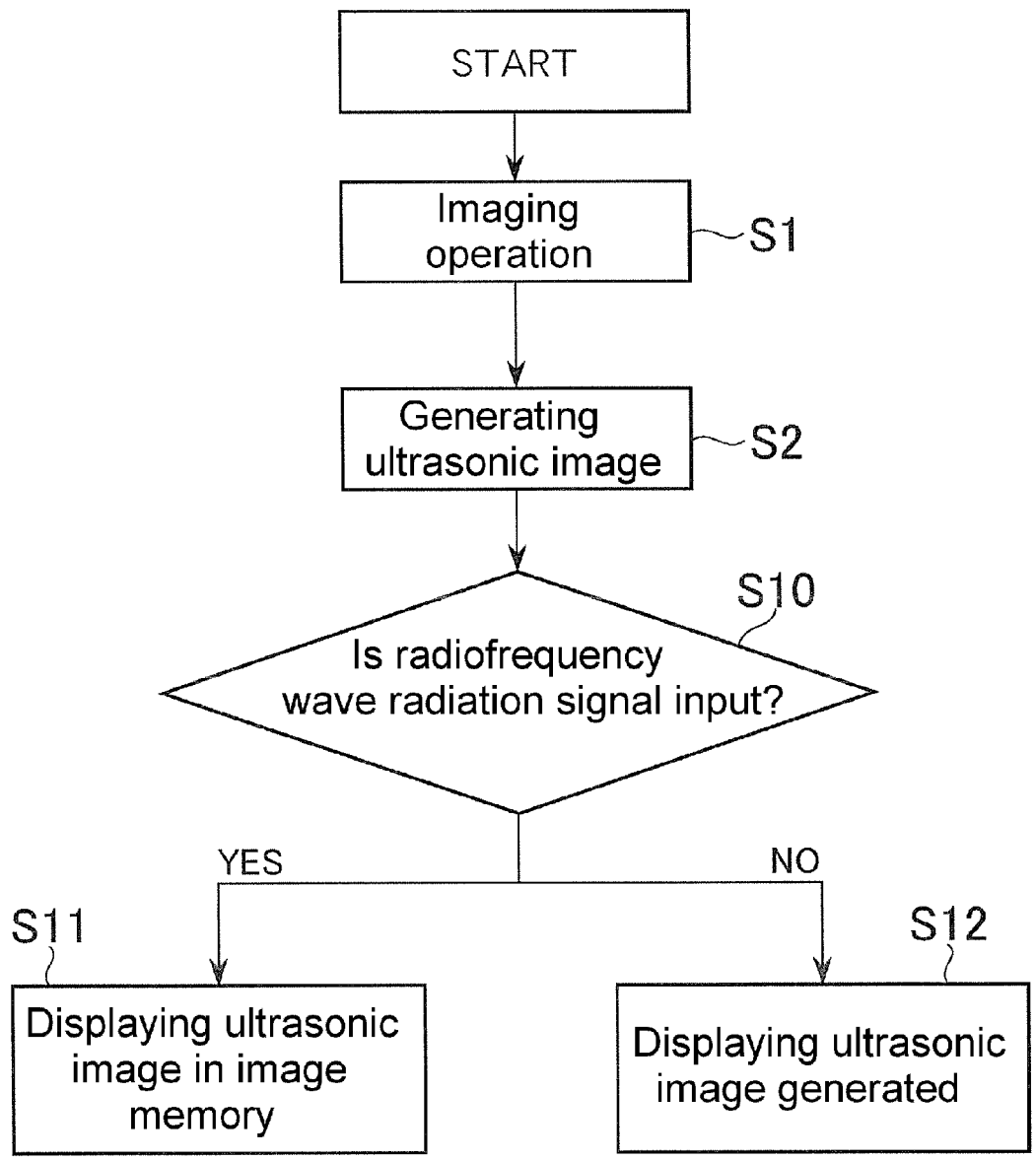
FIG. 8 is a flow chart illustrating the operation of an ultrasonic diagnosis and treatment system in accordance with the second embodiment.

The operation of the ultrasonic diagnosis and treatment system 100 will be described in greater details with reference to FIG. 8. Since the steps S1 and S2 are the identical steps to the first embodiment, the steps S10 to S12 will be described herein below.

The CPU 71 of the image processing unit 7, for the processing of the ultrasonic image generation in step S2, writes down the B-mode image data and each Doppler image data to their respective different area in the image memory 78, thereafter for the processing of the step S10, determines whether or not the radiofrequency wave radiation signals are input from the treatment apparatus side controller unit 107. Then, if the radiofrequency wave radiation signals are input, the CPU 71 proceeds to step S11, where it displays on the display unit 8 the ultrasonic image at the time of non-radiation of the radiofrequency wave of a previous frame that is prior to the ultrasonic image generated in step S2. The ultrasonic image at the time of non-radiation of the radiofrequency wave to be displayed at this step is the image stored in the image memory 78. If the radiofrequency wave radiation signal is not input from the treatment apparatus side controller unit 107 in step S10, then the CPU 71 proceeds to step S12, where the image generated in step S2 will be displayed on the display unit 8.

By iteratively repeating the above steps S1 to S11 or S12, the real time ultrasonic image is displayed on the display unit 8. In this preferred embodiment, preferably, the radiation of the radiofrequency wave from the biopsy needle 104 is intermittently performed so as not to degrade the real time property of the ultrasonic image.

In accordance with the ultrasonic diagnosis and treatment system 100 as have been described above, the CPU 71 displays on the display unit 8 the ultrasonic image at the time of non-radiation of the radiofrequency wave of a previous frame which is the ultrasonic image generated in step S2 if the radiofrequency wave radiation signals is input. Therefore when the ultrasonic image is generated based on the echo signals received by the ultrasonic probe 3 at the time of the radiation of the radiofrequency wave, an ultrasonic image at the time of non-radiation of the radiofrequency wave will be displayed on the display unit 8, in place of the ultrasonic image. By doing this, the degradation of the image quality caused by the radiofrequency wave may be prevented for the ultrasonic image to be displayed on the display unit 8.

Figure 9:
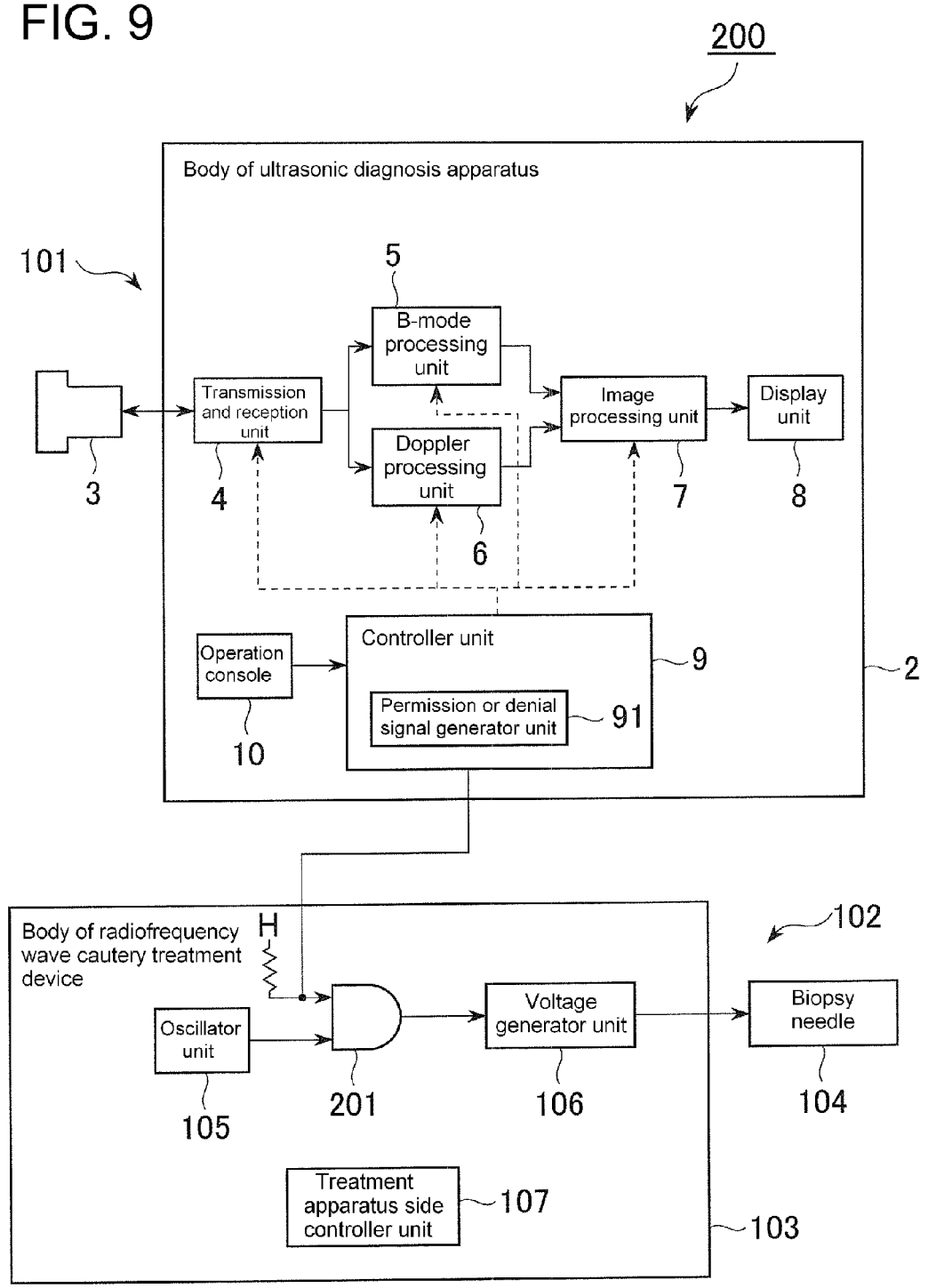
FIG. 9 is a schematic block diagram illustrating the configuration of an ultrasonic diagnosis and treatment system in accordance with a third embodiment.

Next, a third embodiment will be described in greater details with reference to FIG. 9. Now referring to FIG. 9 there is shown a schematic block diagram illustrating the configuration of an ultrasonic diagnosis and treatment system in accordance with the third embodiment.

In the ultrasonic diagnosis and treatment system 200 in accordance with this embodiment, the controller unit 9 of the body of the ultrasonic diagnosis apparatus 2 has a generator unit 91 of the permission or denial signal of the radiation of the radiofrequency wave from the biopsy needle 104. The body of the radiofrequency wave cautery treatment device 103 has an AND circuit 201 in addition to the oscillator unit 105, the voltage generator unit 106, and the treatment apparatus side controller unit 107.

The permission or denial signal generator unit 91 generates a permission signal for the radiation of the radiofrequency wave for permitting to radiate the radiofrequency wave from the biopsy needle 104, and a denial signal for the radiation of the radiofrequency wave for denying radiating the radiofrequency wave from the biopsy needle 104, to output them to the AND circuit 201 of the body of the radiofrequency wave cautery treatment device 103. When the radiofrequency wave radiation permission signal is output from the permission or denial signal generator unit 91, the controller unit 9 outputs to the CPU 71 of the image processing unit 7 the signal indicating that the radiofrequency wave radiation permission signal is output.

Figure 10:
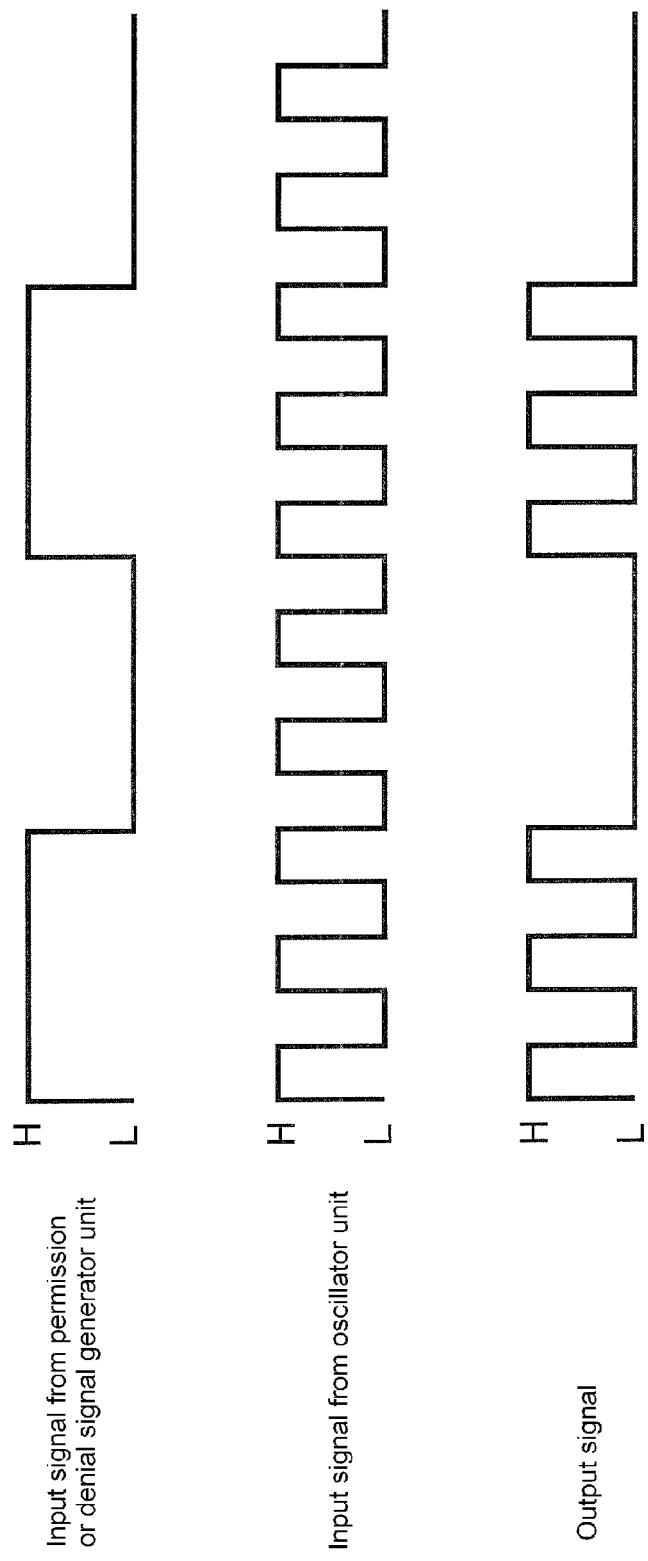
FIG. 10 is a diagram illustrating the signals input and output in the AND circuit shown in FIG. 9.

Now referring to FIG. 10 there is shown an example of the permission or denial signal to be output from the permission or denial signal generator unit 91 and to be input to the AND circuit 201. The permission or denial signal indicates the radiofrequency wave radiation permission signal in its H level and the radiofrequency wave radiation denial signal in its L level. The radiofrequency wave radiation permission signal is the signal to be output when radiating the radiofrequency wave from the biopsy needle 104. The permission or denial signal generator unit 91 that generates and outputs such a radiofrequency wave radiation permission signal is an example of the permission signal generator unit in accordance with the invention.

The radiofrequency wave radiation permission signal and the radiofrequency wave radiation denial signal are alternately output, and as will be described later the ultrasonic image will be generated only when the radiofrequency wave is not radiated from the biopsy needle 104. The length of the output time of these radiofrequency wave radiation permission signal and radiofrequency wave radiation denial signal may be the period of time of the transmission and reception of the ultrasonic waves for one single acoustic ray, or alternatively may be the period of time of the transmission and reception of the ultrasonic waves for a plurality of acoustic rays, for one single frame, or for a plurality of frames. However, it is preferable that these signal output is controlled so as not to degrade the real time property of the ultrasonic image.

In this example the radiofrequency wave radiation instruction pulses, which is output from the oscillator unit 15 of the body of the radiofrequency wave cautery treatment device 6, is input to the AND circuit 201 (the oscillator unit 15 is an example of the preferred embodiment of the radiofrequency wave radiation instruction signal generator unit in accordance with the invention). Furthermore to the AND circuit 201, the permission or denial signal from the permission or denial signal generator unit 91 is also input. The AND circuit 201 will AND the radiofrequency wave radiation instruction pulses and the permission or denial signal to output to the voltage generator unit 106. FIG. 10 shows the signal to be output to the voltage generator unit 106 from the AND circuit 201. As shown in FIG. 10, the AND circuit 201 outputs the radiofrequency wave radiation instruction pulses from the oscillator unit 105 to the voltage generator unit 106 without modification. The voltage generator unit 106, when the radiofrequency wave radiation instruction pulses are input, applies a voltage to the biopsy needle 104 to radiate the radiofrequency wave. Therefore the AND circuit 201 is for radiating the radiofrequency wave from the biopsy needle 104 by outputting the radiofrequency wave radiation instruction pulses only when the radiofrequency wave radiation instruction pulses is input and when the radiofrequency wave radiation permission signal is also input, and is an example of the preferred embodiment of the radiofrequency wave radiation permission unit in accordance with the invention.

On the other hand, the AND circuit 201 will not output the radiofrequency wave radiation instruction pulses if the radiofrequency wave permission or denial signal is input even when the radiofrequency wave radiation instruction pulses are input. Therefore, the radiofrequency wave will not be radiated from the biopsy needle 104.

The body of the radiofrequency wave cautery treatment device 103 has an H level signal generator unit H. When the radiofrequency wave cautery treatment is conducted by only using the radiofrequency wave cautery treatment device 102 without using the ultrasonic diagnosis apparatus 101, the permission or denial signal from the permission or denial signal generator unit 91 will not be input to the AND circuit 201, therefore the signal from the H level signal generator unit H is to be input to the AND circuit 201 instead. In this manner, the radiofrequency wave radiation instruction pulses will be output from the AND circuit 201 so that the radiofrequency wave from the biopsy needle 104 will be enabled to be radiated, enabling the radiofrequency wave cautery treatment with the radiofrequency wave cautery treatment device 102 alone.

Figure 11:
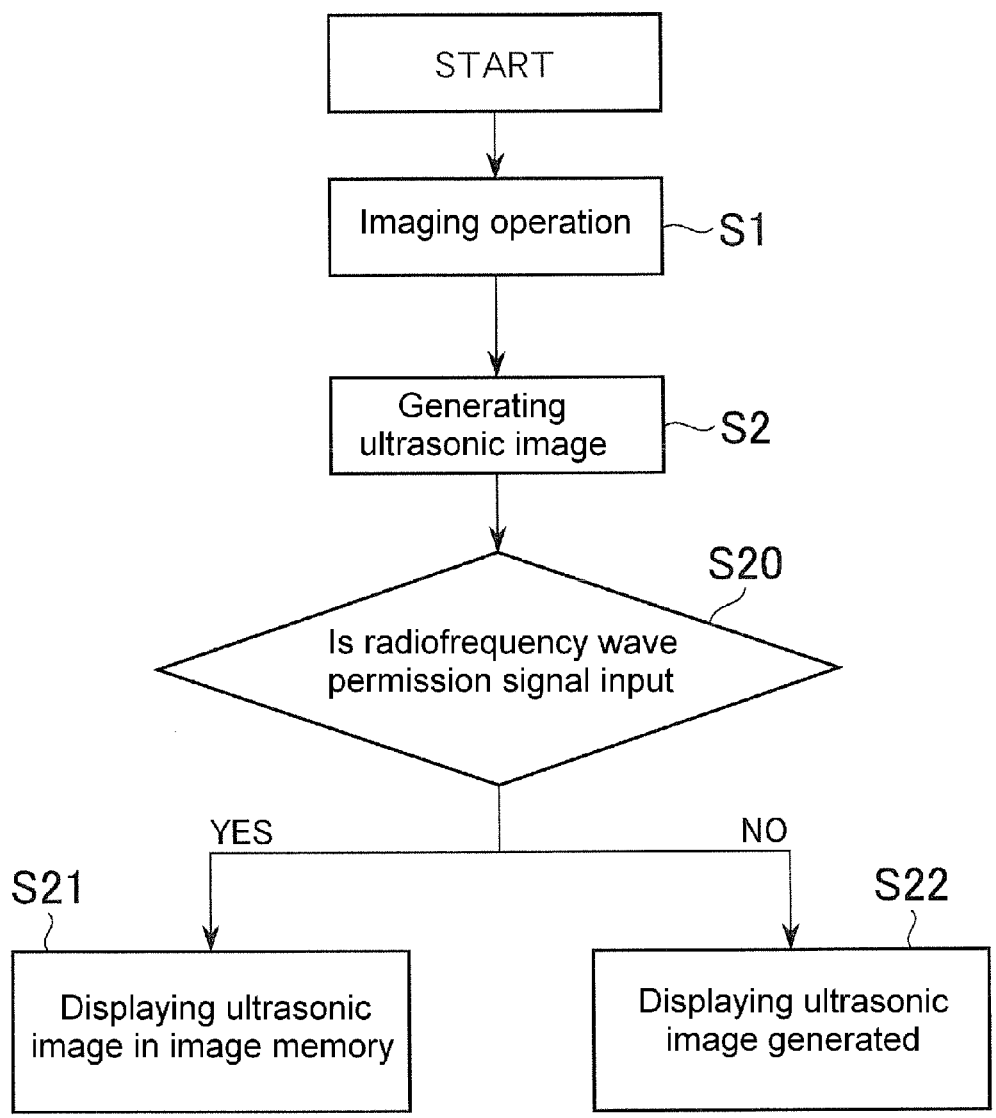
FIG. 11 is a flow chart illustrating an example of the operation of an ultrasonic diagnosis and treatment system in accordance with the third embodiment.

The operation of the ultrasonic diagnosis and treatment system 200 will be described in greater details with reference to FIG. 11. Steps S1 and S2 are the identical steps to those shown in the first and second preferred embodiments, the steps S20 to S22 will be described now.

The CPU 71 of the image processing unit 7, in the processing of the ultrasonic image generation in step S2, writes the B-mode image data and each Doppler image data to their respective different area in the image memory 78, thereafter it determines, in the processing of step S20, whether or not the radiofrequency wave radiation permission signal is output from the permission or denial signal generator unit 91. Thereafter, if the radiofrequency wave radiation permission signal is output, the CPU 71 proceeds to step S21, where the image based on the data of the ultrasonic image at the time of non-radiation of the radiofrequency wave of a previous frame that is prior to the ultrasonic image generated in step S2 will be displayed on the display unit 8. The ultrasonic image at the time of non-radiation of the radiofrequency wave to be displayed at this time is the image stored in the image memory 78. On the other hand, if the radiofrequency wave radiation permission signal from the permission or denial signal generator unit 91 is not output in step S20, more specifically if the radiofrequency wave radiation denial signal is output, then the CPU 71 proceeds to step S22, where the image generated in step S2 will be displayed on the display unit 8.

By iteratively repeating the steps S1 to S21 or S22 as described above, the ultrasonic image on the real time basis will be displayed on the display unit 8. In this embodiment also, preferably, the radiation of the radiofrequency wave from the biopsy needle 104 is performed intermittently, so as not to degrade the real time property of the ultrasonic image.

In accordance with the ultrasonic diagnosis and treatment system 200 as have been described above, the CPU 71 displays on the display unit 8 the ultrasonic image at the time of non-radiation of the radiofrequency wave of a previous frame which is prior to the ultrasonic image generated in step S2 if the radiofrequency wave radiation permission signal is output from the permission or denial signal generator unit 91. Therefore if an ultrasonic image is generated based on the echo signals received by the ultrasonic probe 3 at the time of radiating the radiofrequency wave, an ultrasonic image at the time of non-radiation of the radiofrequency wave in place of the image will be displayed on the display unit 8. In this manner, for the ultrasonic image to be displayed on the display unit 8, the degradation of the image quality caused by the radiofrequency wave may be prevented.

Figure 12:
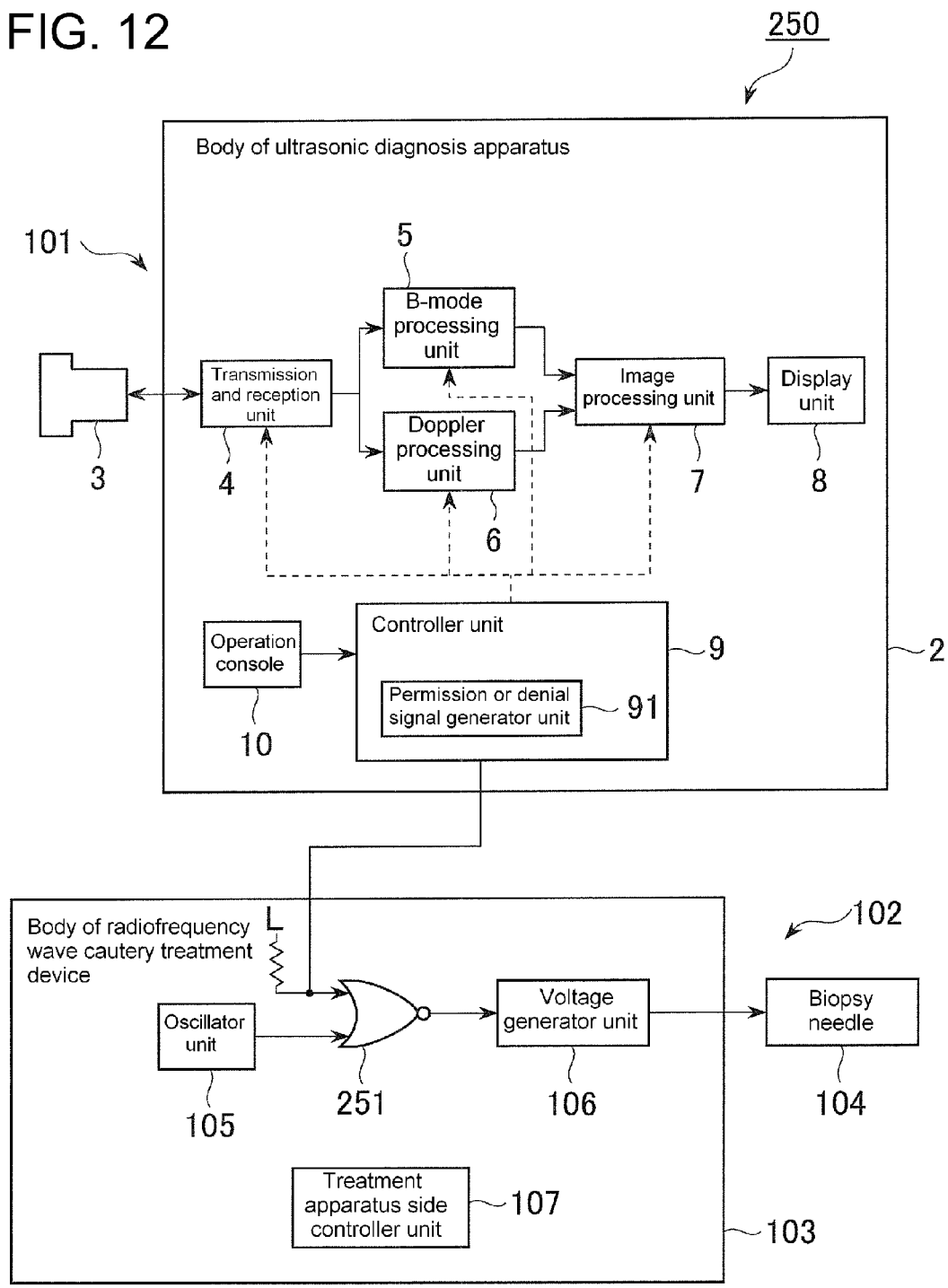
FIG. 12 is a schematic block diagram illustrating the configuration of a variation of the ultrasonic diagnosis and treatment system in accordance with the third embodiment.

Next, a variation of the third embodiment described above will be described. Now referring to FIG. 12 there is shown a schematic block diagram illustrating the configuration of an ultrasonic diagnosis and treatment system in accordance with a variation of the first embodiment. The body of the radiofrequency wave cautery treatment device 103 of the ultrasonic diagnosis and treatment system 250 as shown in FIG. 12 has a NOR circuit 251 in place of the AND circuit 201. The NOR circuit 251 is another example of the embodiment of the radiofrequency wave radiation permission unit in accordance with the invention.

Figure 13:
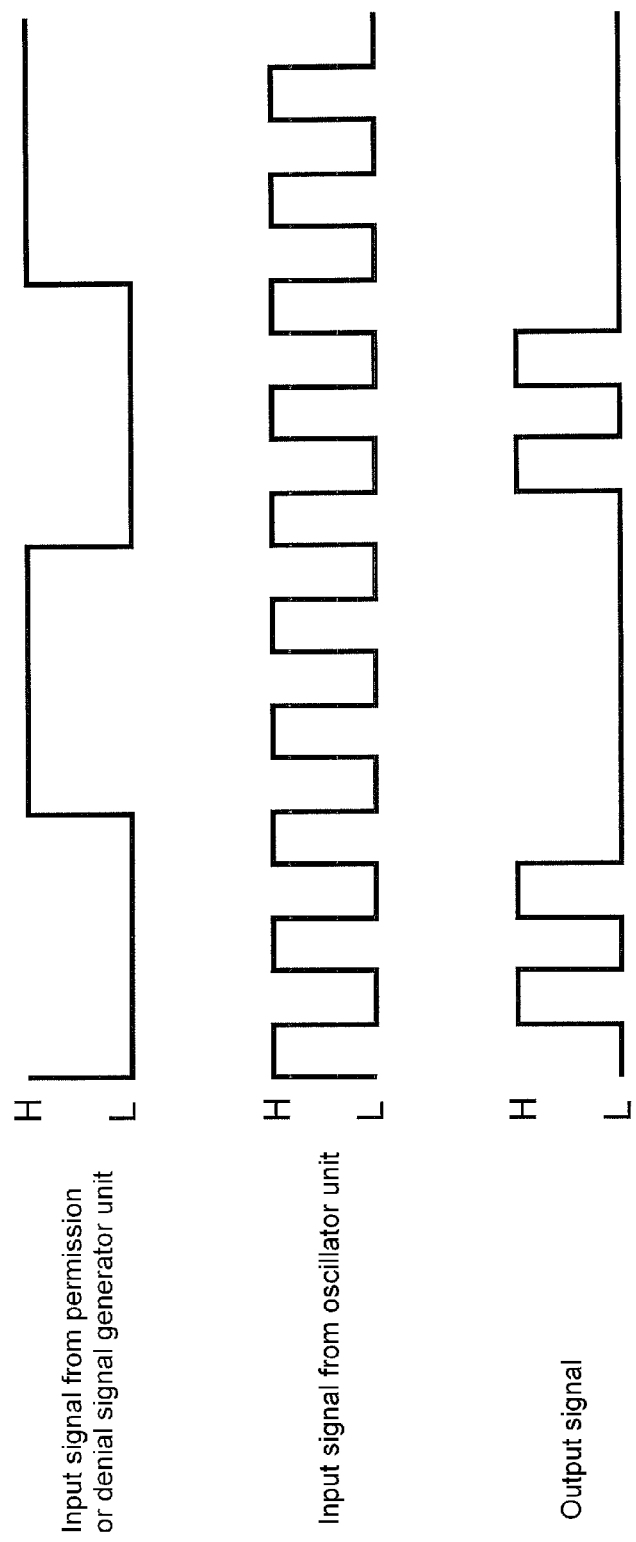
FIG. 13 is a diagram illustrating the signals input and output in the NOR circuit shown in FIG. 12.

In this variation, the permission or denial signal to be output from the permission or denial signal generator unit 91 and to be input to the NOR circuit 251 has a radiofrequency wave radiation permission signal in its L level, and a radiofrequency wave radiation denial signal in its H level. FIG. 13 shows the permission or denial signal of this variation. The NOR circuit 251, as shown in FIG. 13, outputs to the voltage generator unit 106 the inverted radiofrequency wave radiation instruction pulses from the oscillator unit 105 when the radiofrequency wave radiation permission signal in the L level is input. By doing this a voltage is applied to the biopsy needle 104 from the voltage generator unit 106 to permit to radiate the radiofrequency wave.

In the body of the radiofrequency wave cautery treatment device 103 of this variation, by the way, an L level signal generator unit L, in place of the H level signal generator unit H, is provided so that the signal from the L level signal generator unit L will be input to the NOR circuit 251 instead of the permission or denial signal from the permission or denial signal generator unit 91 when the radiofrequency wave cautery treatment is to be conducted without using the ultrasonic diagnosis apparatus 101.

Also in the ultrasonic diagnosis and treatment system 250 as have been described above, as similar to the embodiments described above, the CPU 71 will display on the display unit 8 the ultrasonic image at the time of non-radiation of the radiofrequency wave of a previous frame which is prior to the ultrasonic image generated in step S2 if the radiofrequency wave radiation permission signal is output from the permission or denial signal generator unit 91. As a result, when an ultrasonic image is generated based on the echo signals received by the ultrasonic probe 3 during the radiation of the radiofrequency wave, another ultrasonic image at the time of non-radiation of the radiofrequency wave will be displayed on the display unit 8 in place of the image. In this manner, for the ultrasonic image to be displayed on the display unit 8, the degradation of the image quality caused by the radiofrequency wave may be prevented.

Figure 14:
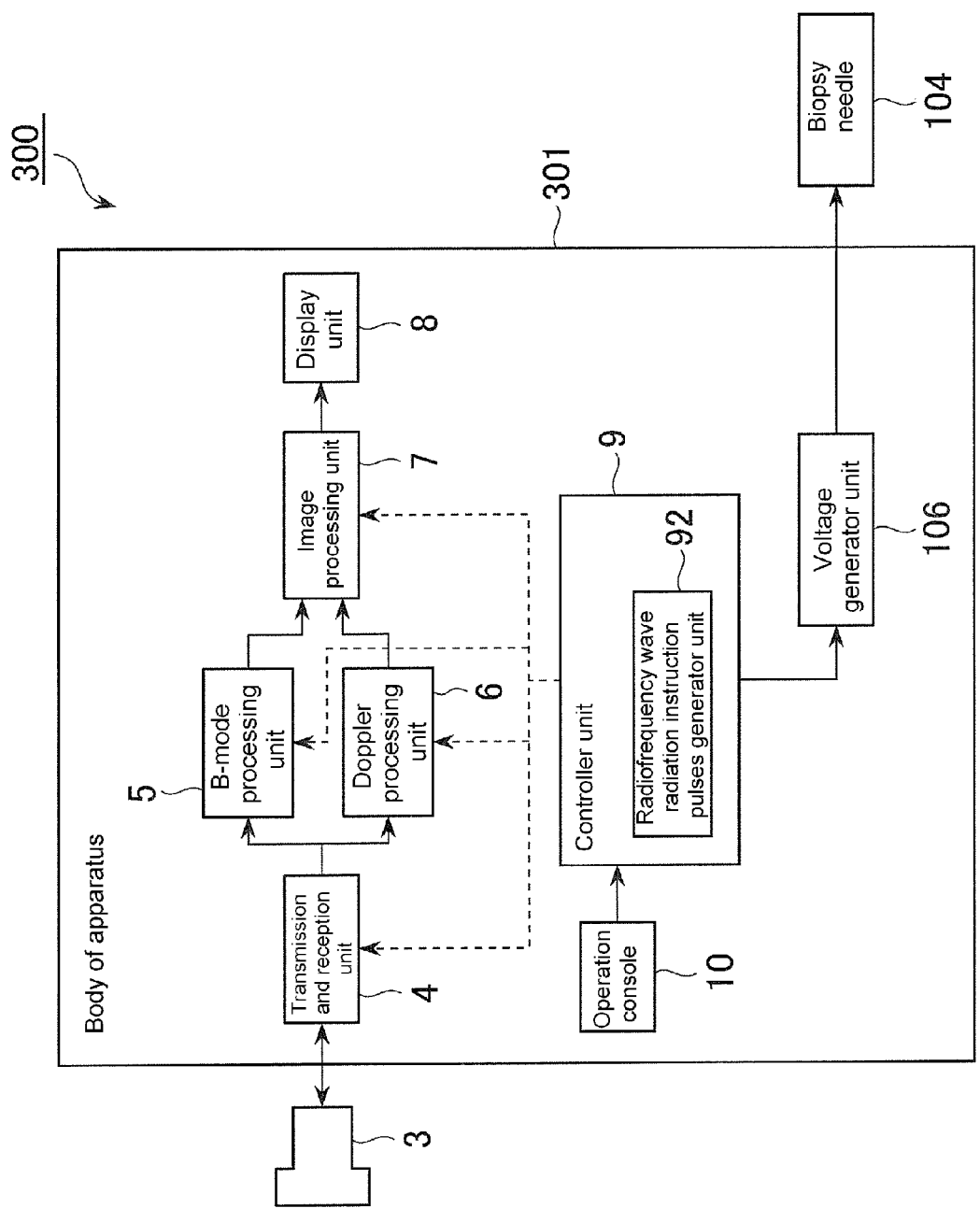
FIG. 14 is a schematic block diagram illustrating the configuration of an ultrasonic diagnosis and treatment apparatus in accordance with a fourth embodiment.

Next, a fourth embodiment will be described in greater details with reference to FIG. 14. FIG. 14 shows a schematic block diagram illustrating the configuration of an ultrasonic diagnosis and treatment apparatus in accordance with the fourth embodiment.

In the fourth embodiment, as shown in FIG. 14, the body of the ultrasonic diagnosis apparatus is integrated with the body of the radiofrequency wave cautery treatment device to form the ultrasonic diagnosis and treatment system as the ultrasonic diagnosis and treatment apparatus 300. More specifically, the ultrasonic diagnosis and treatment apparatus 300 includes the body of the apparatus 301 having the transmission and reception unit 4, the B-mode processing unit 5, the Doppler processing unit 6, the image processing unit 7, the display unit 8, the operation console 10, the controller unit 9 and the voltage generator unit 106, and the ultrasonic probe 3 as well as the biopsy needle 104 both connected to the body of the apparatus 301.

In this embodiment the controller unit 9 does not have the permission or denial signal generator unit 91, but has a generator unit 92 of the radiofrequency wave radiation instruction pulses for radiating the radiofrequency wave from the biopsy needle 104. The radiofrequency wave radiation instruction pulse is an example of the preferred embodiment of the information with respect to the radiofrequency wave radiation in accordance with the invention. The radiofrequency wave radiation instruction pulses generator unit 92 outputs the radiofrequency wave radiation instruction pulses to the voltage generator unit 106. The ultrasonic diagnosis and treatment apparatus 300 of this embodiment does not have the oscillator unit 105 and the AND circuit 201 or the NOR circuit 251, the voltage generator unit 106 applies a voltage to the biopsy needle 104 to radiate the radiofrequency wave when the radiofrequency wave radiation instruction pulses which are output from the radiofrequency wave radiation instruction pulses generator unit 92 are input.

When the radiofrequency wave radiation instruction pulses are output from the radiofrequency wave radiation instruction pulses generator unit 92, the controller unit 9 will output to the CPU 71 of the image processing unit 7 the signal indicating that the output of the radiofrequency wave radiation instruction pulses is present.

Figure 15:
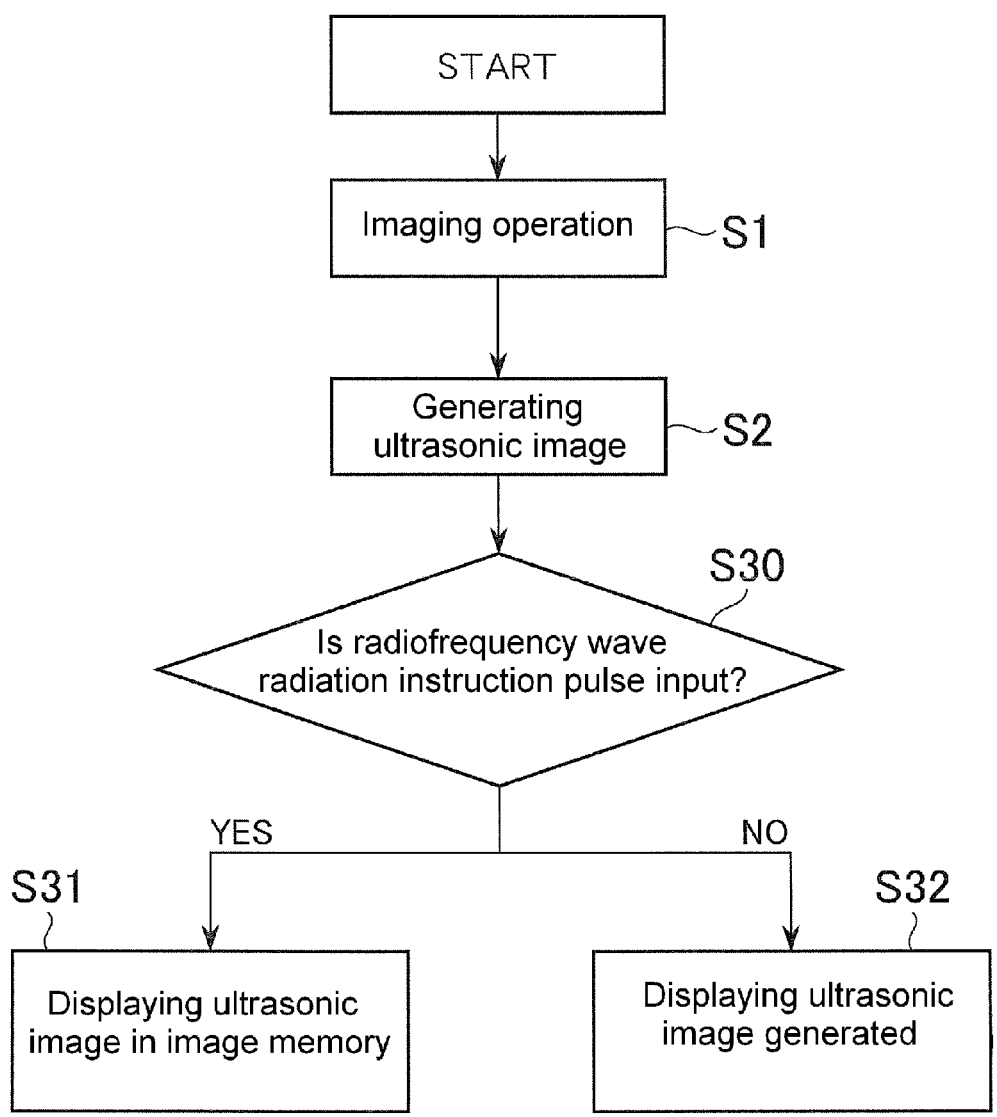
FIG. 15 is a flow chart illustrating an example of the operation of the ultrasonic diagnosis and treatment apparatus in accordance with the fourth embodiment.

Now the operation of the ultrasonic diagnosis and treatment apparatus 300 will be described in greater details with reference to FIG. 15. The steps S1 and S2 are the identical steps to those in the first, second, and third preferred embodiments, only the steps S30 to S32 will be described herein below.

The CPU 71 of the image processing unit 7, in the processing of the ultrasonic image generation in step S2, writes the B-mode image data and each Doppler image data into their respective different area of the image memory 78, thereafter determines, in the processing of step S30, whether or not the radiofrequency wave radiation instruction pulses from the radiofrequency wave radiation instruction pulses generator unit 92 are output. If the radiofrequency wave radiation instruction pulses are output, the CPU 71 proceeds to step S31, where it displays on the display unit 8 the ultrasonic image at the time of non-radiation of the radiofrequency wave of a previous frame which is prior to the ultrasonic image generated in step S2. On the other hand, if the radiofrequency wave radiation instruction pulses are not output from the radiofrequency wave radiation instruction pulses generator unit 92 in step S30, then the CPU 71 proceeds to step S32, where it displays on the display unit 8 the image that is generated in step S2.

By iteratively repeating the above steps S1 to S31 or S32, the ultrasonic image on the real time basis will be displayed on the display unit 8. In this embodiment also, preferably, the radiation of the radiofrequency wave from the biopsy needle 104 is intermittently performed so as not to degrade the real time property of the ultrasonic image.

In accordance with the ultrasonic diagnosis and treatment apparatus 300 as described above, the CPU 71 will display on the display unit 8 the ultrasonic image at the time of non-radiation of the radiofrequency wave of a previous frame which is prior to the ultrasonic image generated in step S2. As a result if an ultrasonic image is generated based on the echo signals received by the ultrasonic probe 3 during the radiation of the radiofrequency wave, then an ultrasonic image at the time of non-radiation of the radiofrequency wave will be displayed on the display unit 8 in place of the image. In this manner for the ultrasonic image to be displayed on the display unit 8, the degradation of the image quality caused by the radiofrequency wave may be prevented.

As can be appreciated from the foregoing description, the invention has been described by way of examples of preferred embodiments, however the invention should not be considered to be limited by these examples, and any modification may be embodied without departing from the scope of the invention. For example, although not specifically shown in the figure, the body of the apparatus 301 as shown in the fourth preferred embodiment may be configured by simply integrating the body of the ultrasonic diagnosis apparatus 101 having the configuration as described above in the second preferred embodiment with the body of the radiofrequency wave cautery treatment device 103. Although not specifically shown in the figure, the body of the apparatus 301 in the fourth preferred embodiment may be configured by simply integrating the body of the ultrasonic diagnosis apparatus 101 having the configuration as have been described above in the third preferred embodiment with the body of the radiofrequency wave cautery treatment device 103.

In addition, in the second preferred embodiment, the radiofrequency wave non-radiation signal indicating that the radiofrequency wave is not radiated may be input from the treatment apparatus side controller unit 107 to the controller unit 9 as the information with respect to the radiation of the radiofrequency wave. In this case if the radiofrequency wave non-radiation signal is input, the CPU 71 will display on the display unit 8 the ultrasonic image which is generated in step S2 of FIG. 8, and if the radiofrequency wave non-radiation signal is not input then it displays on the display unit 8 the ultrasonic image at the time of non-radiation of the radiofrequency wave of a previous frame which is prior to the ultrasonic image generated in step S2.

In addition, in the third preferred embodiment, for the processing in step S20, the CPU 71 may also determine whether or not the output of the radiofrequency wave radiation denial signal is present from the permission or denial signal generator unit 91. In this case, if the output of the radiofrequency wave radiation denial signal is not present, namely the radiofrequency wave radiation permission signal is output, then the process proceeds to step S21. On the other hand, if the radiofrequency wave radiation denial signal is output, then the process proceeds to step S22.

Furthermore, in the fourth preferred embodiment, in the same manner as the first preferred embodiment, it may be also possible that with respect to the ultrasonic image generated in step S2, the CPU 71 determines whether or not the image is an ultrasonic image at the time of radiation of the radiofrequency wave for each frame in step S30, and if the image is the ultrasonic image at the time of non-radiation of the radiofrequency wave then the ultrasonic image will be displayed on the display unit 8. On the other hand, if the image is the ultrasonic image at the time of radiation of the radiofrequency wave, then the ultrasonic image at the time of non-radiation of the radiofrequency wave that is prior to the ultrasonic image generated in step S2 will be displayed on the display unit 8.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic diagnosis apparatus comprising:
    an ultrasonic probe configured to transmit ultrasonic waves and receive echo signals;
    an image generator unit configured to generate an ultrasonic image based on the echo signals received by said ultrasonic probe, the ultrasonic image generated from at least one of B-mode image data and Doppler image data;
    a radiofrequency wave cautery treatment device configured to radiate radiofrequency waves;
    a display unit configured to display the generated ultrasonic image; and
    a display controller unit configured to
        determine, for each frame, based on at least one of the B-mode image data and the Doppler image data, whether the generated ultrasonic image is a radiation ultrasonic image acquired at a time of radiation of the radiofrequency waves and based on the echo signals received by said ultrasonic probe at a time when the radiofrequency waves are radiated by said radiofrequency wave cautery treatment device, or a non-radiation ultrasonic image acquired at a time of non-radiation of the radiofrequency waves and based on the echo signals received by said ultrasonic probe at a time when the radiofrequency waves are not radiated by said radiofrequency wave cautery treatment device; and
        control display of the generated ultrasonic image on said display unit by displaying a non-radiation ultrasonic image in place of the generated ultrasonic image when the generated ultrasonic image is a radiation ultrasonic image.

2. An ultrasonic diagnosis apparatus according to claim 1, wherein:
    said display controller unit is configured to:
        display the generated ultrasonic image on said display unit if the generated ultrasonic image is determined to be a non-radiation ultrasonic image; and
        display a previous frame ultrasonic image on said display unit if the generated ultrasonic image is determined to be a radiation ultrasonic image, wherein the previous frame ultrasonic image is acquired during non-radiation of the radiofrequency waves.

3. An ultrasonic diagnosis apparatus according to claim 1, wherein said display controller unit is configured to:
    determine that the generated ultrasonic image is a radiation ultrasonic image if a mean brightness value of a region of interest in a B-mode image generated by said image generator unit is one of equal to a predetermined value and more than the predetermined value; and
    determine that the generated ultrasonic image is a non-radiation ultrasonic image if the mean brightness value is less than the predetermined value.

4. An ultrasonic diagnosis apparatus according to claim 1, wherein said display controller unit is configured to:
    determine that the generated ultrasonic image is a radiation ultrasonic image if one of a variance value and a power value in a Doppler image generated by said image generator unit is one of equal to a predetermined value and more than the predetermined value; and
    determine that the generated ultrasonic image is a non-radiation ultrasonic image if one of the variance value and the power value is less than the predetermined value.

5. An ultrasonic diagnosis apparatus according to claim 1, wherein:
    said display controller unit is configured to control display of the generated ultrasonic image on said display unit based on information with respect to radiation of radiofrequency waves which is input from said radiofrequency wave cautery treatment device, and to control display of a non-radiation ultrasonic image in place of a radiation ultrasonic image if the generated ultrasonic image is generated based on the echo signals received by said ultrasonic probe at the time of radiation of the radiofrequency waves.

6. An ultrasonic diagnosis apparatus according to claim 5, wherein:
    said radiofrequency wave cautery treatment device is configured to output the information with respect to the radiation of the radiofrequency waves to said ultrasonic diagnosis apparatus.

7. An ultrasonic diagnosis apparatus according to claim 1, further comprising:
    a permission signal generator unit configured to generate a radiofrequency wave permission signal that enables radiation of the radiofrequency waves from said radiofrequency wave cautery treatment device, and to output the radiofrequency wave radiation permission signal to said radiofrequency wave cautery treatment device in order to instruct said radiofrequency wave cautery treatment device to radiate the radiofrequency waves, wherein:
    said display controller unit is configured to control display of a non-radiation ultrasonic image on said display unit based on the echo signals received by said ultrasonic probe at the time of non-outputting the radiofrequency wave radiation permission signal, in place of a radiation ultrasonic image based on the echo signals received by said ultrasonic probe at the time of outputting the radiofrequency wave radiation permission signal.

8. An ultrasonic diagnosis apparatus according to claim 7, comprising:
    a generator unit of a radiofrequency wave radiation instruction signal configured to radiate the radiofrequency waves from a biopsy needle within said radiofrequency wave cautery treatment device; and
    a radiofrequency wave radiation permission unit configured to output the radiofrequency wave radiation instruction signal in order to radiate the radiofrequency waves from said biopsy needle when the radiofrequency wave radiation instruction signal is input from said radiofrequency wave radiation instruction signal generator unit, and when the radiofrequency wave radiation permission signal is input from said permission signal generator unit.

9. An ultrasonic diagnosis and treatment system comprising:

an ultrasonic probe configured to transmit ultrasonic waves and receive echo signals;

an image generator unit configured to generate an ultrasonic image based on the echo signals received by said ultrasonic probe, the ultrasonic image generated from at least one of B-mode image data and Doppler image data;

a display unit configured to display the generated ultrasonic image;

a biopsy needle configured to radiate radiofrequency waves; and a display controller unit configured to:

determine, for each frame, based on at least one of the B-mode image data and the Doppler image data, whether the generated ultrasonic image is a radiation ultrasonic image acquired at a time of radiation of the radiofrequency waves and based on the echo signals received by said ultrasonic probe at a time when the radiofrequency waves are radiated by said radiofrequency wave cautery treatment device, or a non-radiation ultrasonic image acquired at a time of non-radiation of the radiofrequency waves and based on the echo signals received by said ultrasonic probe at a time when the radiofrequency waves are not radiated by said radiofrequency wave cautery treatment device; and control display of the generated ultrasonic image on said display unit by displaying a non-radiation ultrasonic image in place of the generated ultrasonic image when the generated ultrasonic image is a radiation ultrasonic image.

10. An ultrasonic diagnosis and treatment system according to claim 9, further comprising:

an ultrasonic diagnosis apparatus, wherein said ultrasonic probe, said image generator unit, said display unit, and said display controller unit are located within said ultrasonic diagnosis apparatus; and a radiofrequency wave cautery treatment device, wherein said biopsy needle is located within said radiofrequency wave cautery treatment device.

11. An ultrasonic diagnosis and treatment system according to claim 9, wherein:

said display controller unit is configured to:

display the generated ultrasonic image on said display unit if the generated ultrasonic image is determined to be a non-radiation ultrasonic image; and display a previous frame ultrasonic image on said display unit if the generated ultrasonic image is determined to be a radiation ultrasonic image, wherein the previous frame ultrasonic image is acquired during non-radiation of the radiofrequency waves.

12. An ultrasonic diagnosis and treatment system according to claim 10, wherein:

said display controller unit is configured to:

display the generated ultrasonic image on said display unit if the generated ultrasonic image is determined to be a non-radiation ultrasonic image; and display a previous frame ultrasonic image on the display unit if the ultrasonic image is determined to be a radiation ultrasonic image, wherein the previous frame ultrasonic image is acquired during non-radiation of the radiofrequency waves.

13. An ultrasonic diagnosis and treatment system according to claim 9, wherein said display controller unit is configured to:

determine that the generated ultrasonic image is a radiation ultrasonic image if a mean brightness value of a region of interest in a B-mode image generated by said image generator unit is one of equal to a predetermined value and more than the predetermined value; and determine that the generated ultrasonic image is a non-radiation ultrasonic image if the mean brightness value is less than the predetermined value.

14. An ultrasonic diagnosis and treatment system according to claim 9, wherein said display controller unit is configured to:

determine that the generated ultrasonic image is a radiation ultrasonic image if one of a variance value and a power value in a Doppler image generated by said image generator unit is one of equal to a predetermined value and more than the predetermined value; and determine that the generated ultrasonic image is a non-radiation ultrasonic image if one of the variance value and the power value is less than the predetermined value.

15. An ultrasonic diagnosis and treatment system according to claim 10, wherein:

said display controller unit is configured to control display of the generated ultrasonic image on said display unit based on information with respect to radiation of radiofrequency waves which is input from said radiofrequency wave cautery treatment device, and to control display of, in place of the generated ultrasonic image, a non-radiation ultrasonic image if the generated ultrasonic image is generated based on the echo signals received by said ultrasonic probe at the time of radiation of the radiofrequency waves.

16. An ultrasonic diagnosis and treatment system according to claim 10, wherein:

said ultrasonic diagnosis apparatus further comprises a permission signal generator unit configured to generate a radiofrequency wave permission signal that enables radiation of the radiofrequency waves from said radiofrequency wave cautery treatment device, and configured to output the radiofrequency wave radiation permission signal to said radiofrequency wave cautery treatment device in order to instruct said radiofrequency wave cautery treatment device to radiate the radiofrequency waves; and said display controller unit is configured to control said display unit to display a non-radiation ultrasonic image based on the echo signals received by said ultrasonic probe at the time of non-outputting the radiofrequency wave radiation permission signal, in place of a radiation ultrasonic image based on the echo signals received by said ultrasonic probe at the time of outputting the radiofrequency wave radiation permission signal.

17. An ultrasonic diagnosis and treatment system according to claim 16, wherein said radiofrequency wave cautery treatment device comprises:

a generator unit of a radiofrequency wave radiation instruction signal configured to radiate the radiofrequency waves from said biopsy needle; and a radiofrequency wave radiation permission unit configured to output the radiofrequency wave radiation instruction signal to radiate the radiofrequency waves from said biopsy needle when the radiofrequency wave radiation instruction signal is input from said radiofrequency wave radiation instruction signal generator unit, and when the radiofrequency wave radiation permission signal is input from said permission signal generator unit.

18. An ultrasonic diagnosis and treatment apparatus comprising:
a body comprising:
an ultrasonic probe configured to transmit ultrasonic waves and receive echo signals;
a biopsy needle configured to radiate radiofrequency waves connected to said ultrasonic probe;
an image generator unit configured to generate an ultrasonic image based on the echo signals received by said ultrasonic probe, the ultrasonic image generated from at least one of B-mode image data and Doppler image data;
a display unit configured to display the generated ultrasonic image; and
a display controller unit configured to:
determine, for each frame, based on at least one of the B-mode image data and the Doppler image data, whether the generated ultrasonic image is a radiation ultrasonic image acquired at a time of radiation of the radiofrequency waves and based on the echo signals received by said ultrasonic probe at a time when the radiofrequency waves are radiated by said radiofrequency wave cautery treatment device, or a non-radiation ultrasonic image acquired at a time of non-radiation of the radiofrequency waves and based on the echo signals received by said ultrasonic probe at a time when the radiofrequency waves are not radiated by said radiofrequency wave cautery treatment device; and
control display of the generated ultrasonic image on said display unit by displaying a non-radiation ultrasonic image in place of the generated ultrasonic image when the generated ultrasonic image is a radiation ultrasonic image.

19. An ultrasonic diagnosis and treatment apparatus according to claim 18, wherein:
said display controller unit is configured to:
display the generated ultrasonic image on said display unit if the generated ultrasonic image is determined to be a non-radiation ultrasonic image image; and
display a previous frame ultrasonic image on said display unit if the generated ultrasonic image is determined to be a radiation ultrasonic image, wherein the previous frame ultrasonic image is acquired during non-radiation of the radiofrequency waves.

20. An ultrasonic diagnosis and treatment apparatus according to claim 18, wherein:
said display controller unit is configured to control display of the generated ultrasonic image on said display unit based on information with respect to radiation of radiofrequency waves, and to control display of, in place of the generated ultrasonic image, a non-radiation ultrasonic image if the generated ultrasonic image is generated based on the echo signals received by said ultrasonic probe at the time of radiation of the radiofrequency waves.

* * * * *